US006207408B1

(12) United States Patent
Essenfeld et al.

(10) Patent No.: US 6,207,408 B1
(45) Date of Patent: Mar. 27, 2001

(54) HIGH QUALITY, CONTINUOUS THROUGHPUT, TISSUE FIXATION-DEHYDRATION-FAT REMOVAL-IMPREGNATION METHOD

(75) Inventors: Ervin Essenfeld; Harold Essenfeld, both of Caracas (VE); Azorides Morales, Miami, FL (US)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 09/136,292

(22) Filed: Aug. 19, 1998

Related U.S. Application Data

(60) Provisional application No. 60/056,102, filed on Aug. 20, 1997.

(51) Int. Cl.[7] .................................................. G01N 1/30
(52) U.S. Cl. ..................................... 435/40.5; 435/40.52
(58) Field of Search ............................... 435/40.5, 40.51, 435/40.52, 173; 436/60; 219/751

(56) References Cited

U.S. PATENT DOCUMENTS

| | | | |
|---|---|---|---|
| 3,674,040 | * 7/1972 | Howells et al. | 134/58 R |
| 3,892,197 | 7/1975 | Kinney | 118/7 |
| 3,961,097 | 6/1976 | Gravlee | 427/2 |
| 4,141,312 | 2/1979 | Louder | 118/7 |
| 4,656,047 | 4/1987 | Kok | 427/2 |
| 4,670,386 | * 6/1987 | Sugaar | 435/29 |
| 4,839,194 | * 6/1989 | Malluche et al. | 427/2 |
| 5,023,187 | 6/1991 | Koebler | 436/180 |
| 5,049,510 | 9/1991 | Repasi | 436/176 |
| 5,089,288 | 2/1992 | Berger | 427/4 |
| 5,104,640 | 4/1992 | Stokes | 424/3 |
| 5,244,787 | 9/1993 | Key | 435/7.9 |
| 5,431,952 | 7/1995 | Ocello | 427/4 |
| 5,432,056 | 7/1995 | Hartman | 435/7.21 |
| 5,460,797 | 10/1995 | Ryan | 435/40.5 |
| 5,679,333 | 10/1997 | Dumphy | 424/75 |

FOREIGN PATENT DOCUMENTS

| | | | |
|---|---|---|---|
| 0 822 403 B1 | 2/1998 | (EP) | G01N/1/30 |
| WO98/05938 | 2/1998 | (WO) | G01N/1/30 |

OTHER PUBLICATIONS

Möller et al. Chemical dehydration for rapid paraffin embedding. Biotechnic and Histochemistry 69 (5), pp. 289–290. (1994). No Month found.*
Technical Description; The Leitz 1512 Rotary Microtome No date.
Tissue Float Bath; Shandon Lipshaw; Microtomy & Cryotomy; Catalog p. 129 no date.
Nuova II Magnetic Sterrers; Fisher Scientific Products Catalog; p. 1761; no date.
DRS–601–Automatic Slide Stainers; Fisher Scienific Products Catalog; p. 548; no date.
Tissue–Tek Cover Slipper; Fisher Scientific Products Catalog; p. 549; no date.
Microwave For Histology Laboratories; Clinical Lab Products; p. 14; Feb. 1997.
Boon et al; The Two–Step Vacuum–Microwave Method For Histoprocessing; Microwave Newsletter; Nov. 1995; 33(4); pp 349–358.
16 Biotechnology Law Report 478; "Biogenex Victorious In Infringement Suit"; Biotek Automated Tissue Stainer . . . Antigen Retrieval Pretreatment; No. 4, Jul.–Aug. 1997.
Sakura Tissue–Tek VIP Vacuum Infiltration Processor Series; Pamphlet; 1996.
Shandon Lipshaw Catalog; "Biopsy Bags"; Collection Bags to hold and protect specimens during histological processing; Catalog; No date p. 91.
Shandon Lipshaw Catalog; "Biopsy Sponges"; No date p. 87.
Mutlwax Microcyrstalline Waxes From Sonneborn: The Standard Of The Industry; WITCO Pamphlet; no date.
Sonneborn White Oils: The Clear Choice Since 1903; WITCO Pamphlet; 1987.
How Do You Make Staining And Coverslipping Easier, Fast And More Reliable?; Sakura Finetek USA Inc. And Baxter Pamphlet 1995.
Paraffin Tissue Processor—HMP 300; Microm; Carl Zeiss, Inc. Pamphlet; no date.
Fume Adsorbers: Catalog; p. 416; no date.
INCU–Shaker Dubnoff Metabolic Shaking Incubator; catalog; p. 1125; no date.
H2800 Microwave Processor; Energy Beam Sciences; catalog; no date.
H2500 Microwave Processor; Energy Beam Sciences; catalog; no date.
Poly Science Water Baths; Fisher Scientific Products catalog; p. 151; no date.
Gas Pressure/Vacuum Pumps; Fisher Scientific Products catalog; p. 1458; no date.
Tissue–Tek Tissue Embedding Console System; Fisher Scientific Products catalog; p. 537; no date.
Blue M Ovens—Gravity Convection Ovens; Fisher Scientific Products catalog; p. 1268; no date.
Kok et al; Ultrarapid Vacuum–Microwave Histoprocessing; Histochemical Journal 27, pp411–419 (1995).

(List continued on next page.)

Primary Examiner—Ardin H. Marschel
Assistant Examiner—Marjorie A. Moran
(74) Attorney, Agent, or Firm—Pillsbury Madison & Sutro LLP

(57) ABSTRACT

A process and apparatus for rapid, continuous flow histological processing of tissues is disclosed. The steps of fixation, dehydration, clearing and impregnation are performed in less than one hour; this allows a pathologist to evaluate samples shortly after receipt, perhaps while the patient is still in the operating room. Rapid and continuous processing is accomplished by decreasing the thickness of tissue sections, use of non-aqueous solutions composed of admixtures of solutions, solution exchange at elevated temperature and with agitation, and impregnation under vacuum pressure. The patient in surgery is thus provided with point-of-care surgical pathology.

40 Claims, 9 Drawing Sheets

OTHER PUBLICATIONS

Shandon/Lipshaw Histology and Cytology Consumables Catalog; Nov. 1995.

Shandon/Lipshaw Pathcentre Enclosed Tissue Processor Product Brochure; Jun. 1995.

Shandon/Lipshaw Laboratory Equipment Catalog 1997.

Shandon Hypercenter XP Pamphlet; Oct. 1994.

Shandon Linistain SLS Random Access Slide Stainer Pamphlet; 1989.

Shandon Sequenza Immunostaining Center Pamphlet; 1990.

Shandon/Upshaw Varistain 24–4 Flexible, Efficient Automatic Slide Stainer Pamphlet; 1991.

Zabkova et al "Acceleration Of Histologic Tissue Processing And Decalcification Using A Microwave Oven", Orv. Hetil; Jul. 1996; 137(27) pp 1479–1483 Abstract Ony.

Kovacs et al; "Experiences With A New Vacuum–Accelerated Microwave Histoprocessor", J Pathol; Sep. 1996; 180(1): pp 106–110, Abstract Only.

Kovacs et al "Working Experience With A New Vacuum–Accelerated Microwave Histoprocessor"; Acta Cytol; Mar. 1997; 41(2): pp 610–611, Abstract Only.

Database BIOSIS on STN, Accession No. 94:501327, Moeller et al" Chemical Dehydration For Rapid Paraffin Embedding" Biotechnic and Histochemistry; 1994; Vol 69, No. 5, pp 289–290 Abstract only.

* cited by examiner

FIG. 1

THE PRACTICE OF SURGICAL PATHOLOGY
Conventional Pathway From Surgery to Tissue Diagnosis

DAY 1

Surgery ⟶ "grossing" ⟶ batching of specimens ⟶ batched specimens input into processor ⟶ overnight processing

DAY 2

Batched specimens output from processor ⟶ block ⟶ microtomy ⟶ H&E stain ⟶ diagnosis

INTERVAL OF TIME FROM SURGERY TO DIAGNOSIS:>22 HOURS

FIG. 2

THE PRACTICE OF SURGICAL PATHOLOGY
Continuous Throughput Method-Pathway From Surgery
to Tissue Diagnosis

DAY 1

Surgery ⟶ "grossing" ⟶ continuous every 15 min specimens input into 45 min processing system ⟶ continuous every 15 min output of specimens from system ⟶ block ⟶ microtomy ⟶ H&E stain ⟶ diagnosis

INTERVAL OF TIME FROM SURGERY TO
DIAGNOSIS:<2 HOURS

HIGH QUALITY, CONTINUOUS THROUGHPUT, TISSUE FIXATION-DEHYDRATION-FAT REMOVAL-IMPREGNATION METHOD

RELATED APPLICATIONS

This application claims the benefit of U.S. Provisional Appln. Ser. No. 60/056,102, filed Aug. 20, 1997, the entire disclosure of which is incorporated herein by this reference.

BACKGROUND OF THE INVENTION

1. Field of the Invention

The present invention relates to the rapid, continuous flow, processing of tissue for microscopic examination, from fixation to impregnation.

2. Description of the Related Art

Conventional methods prepare tissues for histology by incubation in separate solutions of phosphate-buffered 10% formaldehyde for fixation, a series of increasing concentrations of ethanol for dehydration, and xylene for clearing tissue of dehydration agent, prior to impregnation. Because of the time required for this process, usually 8 hours or longer, it is customary to complete these separate steps— fixation, dehydration, clearing, and impregnation— overnight in automated mechanical instruments designed for those tasks (see, for example, U.S. Pat. Nos. 3,892,197, 4,141,312, and 5,049,510). A typical automated tissue processor (TISSUE-TEK) requires more than eight hours and is programmed to process batches of tissue samples as follows.

the waste of using large volumes of reagents for such processing when automated. Moreover, expensive measures are required to prevent exposure of laboratory personnel to fumes and toxic substances associated with the reagents used in this process. Also, the large volumes of solvent waste and paraffin debris produced by conventional methodology pollute the environment.

Conventional fixation and processing cause irreversible damage to the structure of DNA and particularly RNA that limits the application of genetic techniques for diagnosis and research. Consequently, most DNA and certainly RNA analysis require special precautions with handling of material, such as immediate freezing of fresh tissues, because retrospective genetic analysis is impaired by conventional tissue processing techniques.

Histological diagnosis of a frozen section suffers from multiple disadvantages in comparison to sections prepared from paraffin blocks: the slide prepared from a frozen section "does not possess . . . uniformity of quality"; "it is technically more difficult for serial sections of the same specimen to be examined"; "extreme caution must be exercised in cutting the specimen in order to ensure a sufficiently thin section and to avoid the possibility of damaging details of the specimen"; and all the slides must be prepared "while the tissue is in the initial frozen state" because, "[i]f the tissue is thawed and refrozen for sectioning, it is severely damaged" (U.S. Pat. No. 3,961,097).

There is an ever present interest in expediting tissue processing and analysis for diagnostic purposes. Furthermore, recent healthcare focus has been directed to lessening the cost of various procedures including tissue

| Station | Solution | Concentration | Set Time (min) | Set Temperature | P/V** | Agitation | Volume of Solution |
|---|---|---|---|---|---|---|---|
| 1 | Buffered Formalin | 10% | 50 | 40° C. | On | On | 2.2–3.2 liters |
| 2 | Buffered Formalin | 10% | 50 | 40° C. | On | On | 2.2–3.2 liters |
| 3 | Alcohol* | 80% | 50 | 40° C. | On | On | 2.2–3.2 L |
| 4 | Alcohol | 95% | 50 | 40° C. | On | On | 2.2–3.2 L |
| 5 | Alcohol | 95% | 50 | 40° C. | On | On | 2.2–3.2 L |
| 6 | Alcohol | 100% | 50 | 40° C. | On | On | 2.2–3.2 L |
| 7 | Alcohol | 100% | 50 | 40° C. | On | On | 2.2–3.2 L |
| 8 | Alcohol | 100% | 50 | 40° C. | On | On | 2.2–3.2 L |
| 9 | Xylene | 100% | 50 | 40° C. | On | On | 2.2–3.2 L |
| 10 | Xylene | 100% | 50 | 40° C. | On | On | 2.2–3.2 L |
| 11 | Paraffin | | 50 | 60° C. | On | On | 4 |
| 12 | Paraffin | | 50 | 60° C. | On | On | 4 |
| 13 | Paraffin | | 50 | 60° C. | On | On | 4 |
| 14 | Paraffin | | 50 | 60° C. | On | On | 4 |

**pressure/vacuum cycle
*the alcohol used in most laboratories is a mixture of 90% ethyl, 5% methyl and 5% isopropyl alcohol.

Such conventional methodology demands that the tissue specimens be sent from the operating room, medical office or other sites, to a pathology laboratory on one day; the tissue specimens be prepared overnight; and the pathologist render a diagnosis based on microscopic examination of tissue sections the next day at the earliest, almost 24 hours after delivery of the specimen to the laboratory (FIG. 1). In addition to the minimum one-day delay in giving a surgeon the benefit of a report from the pathologist, there are also problems associated with impeded work flow in the pathology laboratory necessitated by the requisite batch processing of specimens, the safety concerns that attended having instruments operating overnight, the risk of possible instrument failures and the need to monitor the instruments, and processing. The costs of tissue processing are related to time, the space required for preparation and analysis, reagents (both the amount required for processing and handling discard), and the number of personnel required. More importantly, patients and their physicians depend on evaluation and diagnosis by the pathologist to guide treatment. Reducing the amount of time needed to complete tissue processing would lessen the anxiety experienced during the period between obtaining the specimen and delivering the pathologist's report to the surgeon.

Others have recognized the need to shorten the time required for tissue processing, but they have made only modest improvements in the conventional methods. To accelerate tissue processing, U.S. Pat. Nos. 4,656,047, 4,839,194, and 5,244,787 use microwave energy; U.S. Pat. Nos. 3,961,097 and 5,089,288 use ultrasonic energy; and U.S. Pat. No. 5,023,187 uses infrared energy. U.S. Pat. No. 5,104,640 disclosed a non-aqueous composition of a fixative, a stabilizing agent, and a solubilizing agent that adheres a blood smear to a slide. However, the aforementioned patents do not teach or suggest that the entire process of preparing diagnostic tissue slides could be accomplished in less than two hours, starting from fixation and ending with impregnation, with continuous throughput of samples. The present invention provides such a process.

SUMMARY OF THE INVENTION

It is an object of the invention to provide compositions for tissue processing and an apparatus and system for utilizing the same that reduces the time required for tissue processing and analysis, and reduces the cost thereof by reducing time, the size of the laboratory facility, the volumes of reagents used, and the number of personnel required. This allows conversion of existing practice to rapid response surgical pathology for the patient undergoing an operation, and may even allow point-of-care diagnosis by the pathologist in the vicinity of the operating room.

With regard to the processing and analysis of solid tissue, a tissue slice must be on the order of 4 to 6 microns to be examined under a microscope, whereas the thinnest slice of fresh tissue that can be obtained by cutting is about 1 mm with the typical slice being on the order of 3 mm. In order to produce a sufficiently thin slice from microscopic examination, it is necessary to harden the tissue so that a finer slice can be obtained, e.g., by sectioning with a microtome. The present invention greatly accelerates the tissue hardening process and thus turns the conventional overnight processing into a process which totals on the order of 40 minutes. Thus, we have developed a simple, safe, low cost, expeditious, and reliable method that permits preparation of impregnated tissue blocks suitable for microtome sectioning in less than two hours from the moment tissue is received in the pathology laboratory. This method allows continuous flow of specimens, is adaptable to automation, precludes the need for formalin and xylene with their noxious fumes, allows standardization of tissue processing, and requires considerably smaller volumes of reagents than conventional methods. Either fresh or previously fixed tissues can be processed by the present invention.

In addition to the reduction in time required for tissue processing, the rapid preparation of tissue by the present invention is capable of preserving tissue structures and morphology that were lost with conventional methods.

Moreover, studies with tissues processed with the invention disclosed herein indicate better preservation of DNA and particularly RNA extraction than with conventional processing methods. Thus, tissues obtained in hospitals and other settings can be processed for both histologic and genetic studies soon after delivery to the laboratory, and archival material may be made available for future research and other applications. Improvements may be expected in the yield of genetic material, the stability of the genetic material in archival form, the size and integrity of the genetic material, and reducing chemical modification of the genetic material in comparison to the prior art.

An object of the invention is to provide a method and an apparatus for rapid processing of tissue for histology with continuous throughput. By "continuous throughput," we mean accessing the system with additional samples, minutes apart. Therefore, at any given time there are samples of tissue in different stages of processing. In other words, with our method, there is continuous throughput and flow of specimens along the various steps of tissue processing. In contrast with our method, batch processing is presently required because conventional methodology takes eight hours or longer. Samples are placed in automated instruments, which can not be access with additional samples until the entire instrument cycle is completed. All these tissue samples are at the same stage of processing at any given step of the instrument cycle.

Yet another object of the invention is to provide non-aqueous reagents for rapid, continuous flow processing of tissue for histology.

A further object of the invention is to eliminate the need for toxic substances such as formalin and xylene in tissue processing.

In accordance with one aspect of the invention, a tissue specimen is fixed, dehydrated, and fat is removed. A suitable admixture for use is a non-aqueous solution comprised of fixative and dehydrating agents, preferably a ketone and an alcohol; the volume ratio of alcohol to ketone may be between about 1:1 to about 3:1. The tissue specimen is incubated for about 25 minutes or less, more preferably for about 15 minutes or less, and even more preferably for about 5 minutes or less. Incubation is preferably between about 30° C. and 65° C., more preferably between about 40° C. and 55° C., and most preferably between about 45° C. and 50° C.

Another aspect of the invention is fixation, dehydration, fat removal, and clearing of a tissue specimen. A preferred solution in this aspect of the invention is alcohol and a clearant. This process may be accomplished in about 5 minutes or less.

In yet another aspect of the invention, a tissue specimen is cleared and impregnated in a single solution comprised of a clearant and an impregnating agent. Preferably, this process may be accomplished in about 5 minutes or less. Prior to sectioning, the impregnated tissue specimen may be embedded in the impregnating agent.

A tissue specimen which has been fixed, dehydrated, and defatted may then be impregnated in a wax solution. Consistent with dehydration of the tissue specimen, the wax solution is preferably as low as possible in water content. Thus, the wax solution may be prepared prior to impregnation by heating the wax to evaporate any dissolved water and by degassing under reduced pressure. Impregnation of the tissue specimen may take place under less than atmospheric pressure and at elevated temperature to remove any solvents from the tissue specimen and to draw the wax solution into the tissue specimen. Vacuum decreases impregnation time by accelerating diffusion and reducing the evaporation temperature of any solvents that may be present in the sample. The wax solution may comprise degassed paraffin and/or mineral oil. Impregnation of the tissue specimen may be completed in about 15 minutes or less; preferably, completed in about 10 minutes or less. Prior to sectioning, the impregnated tissue specimen may be embedded in the impregnating agent to form a tissue block.

Another embodiment of the invention is processing a tissue specimen from fixation to impregnation in a series of solutions, at least some of which are admixtures that perform more than one task at the same time: fixation, dehydration, removal of fat, and impregnation. The admixture may include a fixative, a dehydrating agent, and a fat solvent (e.g., ketone and alcohol). Another solution may include fixative, dehydrating agent, fat solvent, and clearant (e.g., alcohol and xylene). Yet another solution may include a clearant and an impregnating agent (e.g., xylene and paraffin). The tissue specimen may be impregnated in a wax solution comprised of a mixture of different chain lengths (e.g., at room temperature, mineral oil which is liquid and paraffin which is solid). Preferably, an admixture contains at least two different chemicals (e.g., two alcohols).

Processing time may be reduced by a non-aqueous admixture (e.g., fixative-dehydrating agent-fat solvent, fixative-dehydrating agent-fat solvent-clearant, clearant-impregnating agent), microwave energy as a source to achieve uniform heating within the tissue specimen, and reducing the pressure by using a vacuum source. Diffusion of the solution into the tissue specimen and chemical exchange may be promoted by mechanical agitation, heat, reduced pressure, or a combination thereof.

The above steps may be accelerated by adding a fixative enhancer, a surfactant, or both to the solutions used in the process. The fixative enhancer may be polyethylene glycol (PEG), mono- and dimethyleneglycol, propylene glycol, polyvinyl pyrrolidone, or the like; the polymer used may be between about 100 and about 500 average molecular weight, preferably about 300 molecular weight. The surfactant may be dimethyl sulfoxide (DMSO), polyoxyethylene sorbitan esters (e.g., TWEEN 80), sodium dimethyl sulfosuccinate, mild household detergents, or the like.

The fixative may be a ketone (e.g., acetone, methyl ethyl ketone), aldehyde (e.g., acetylaldehyde, formaldehyde, glutaraldehyde, glyoxal), alcohol (e.g., methanol, ethanol, isopropanol), acetic acid, lead acetates and citrate, mercuric salts, chromic acid and its salts, picric acid, osmium tetroxide, or the like.

The tissue specimen may be dehydrated with methyl alcohol, isopropyl alcohol, ethyl alcohol, propyl alcohol, butanol, isobutanol, ethyl butanol, dioxane, ethylene glycol, acetone, amyl alcohol, or the like.

Fat may be removed from the tissue specimen with an organic solvent such as, for example, acetone, chloroform or xylene.

The clearant may be xylene, limonene, benzene, toluene, chloroform, petroleum ether, carbon bisulfide, carbon tetrachloride, dioxane, clove oil, cedar oil, or the like.

The tissue specimen may be impregnated and/or embedded in paraffin, mineral oil, non-water soluble waxes, celloidin, polyethylene glycols, polyvinyl alcohol, agar, gelatin, nitrocelluloses, methacrylate resins, epoxy resins, other plastic media, or the like.

In the context of the invention, a "tissue specimen" is a piece of tissue that may be processed by the methods disclosed herein. It may also refer to single cells from any biological fluid (e.g., ascites, blood, pleural exudate), or cell suspensions obtained from aspiration of solid organs or lavage of body cavities. Single cells may be pelleted by sedimentation or buoyant centrifugation prior to processing.

The methods of the invention are specially suitable for tissue specimens in which cell—cell contact, tissue organization, organ structure, or a combination thereof must be preserved. Such a specimen is a tissue slice preferably about 3 mm or less in its smallest dimension, more preferably about 2 mm or less, even more preferably about 1.5 mm or less, and most preferably about 1 mm or less.

The tissue specimen may be fresh, partially fixed (e.g., fixation in 10% formalin for 2–3 hours), or fixed (e.g., overnight fixation in 10% formalin or any other fixative). The above invention allows processing of a tissue specimen from fixation to impregnation in less than about two hours, preferably less than about 90 minutes, more preferably less than about one hour, even more preferably less than about 45 minutes, and most preferably less than about 30 minutes. If the tissue specimen is fixed or partially fixed, then the processing time may be shortened accordingly. Tissue may be transported from the operating room to the pathology laboratory in an aqueous solution; such a transport solution may consist of equal volumes of an aqueous buffer and the non-aqueous admixture described herein.

Following impregnation, the tissue specimen can be embedded to produce a block. The agent used to embed the tissue specimen is preferably the same as the material used for impregnation, but a different impregnating agent may also be used. The blocked tissue specimen can be mounted on a microtome to produce tissue sections of between about 1 micron and about 50 microns, preferably between about 2 microns and about 10 microns. The tissue sections may be further processed for histochemical staining, antibody binding, in situ nucleic acid hybridization/amplification, or a combination thereof. The tissue specimens are then typically examined by microscopy, but other techniques for detecting cellular properties may be used to examine the processed tissue specimen (e.g., automated cytometry, autoradiography, electrophoresis of nucleic acid).

BRIEF DESCRIPTION OF THE DRAWINGS

FIG. 1 is a flow chart showing that almost 24 hours elapse between the time a tissue specimen is obtained by a surgeon and the time a diagnosis by a pathologist can be prepared from microscopic examination of sections of the tissue;

FIG. 2 is a flow chart showing that with the present invention, diagnosis by the pathologist can be made available to the surgeon who provided the tissue specimen in about 2 hours or less;

In FIG. 13A, lane 1 contains molecular weight standards, lane 2 contains a diluted sample from a tissue specimen processed according to the present invention, lanes 3–4 contain DNA samples from tissue specimens processed according to the present invention, and lanes 5–6 contain DNA samples from tissue specimens processed according to a conventional method. In FIG. 13B: lanes 1, 4 and 6 are blanks, lanes 2–3 are samples from tissue specimens processed according to a conventional method, lane 5 contains an RNA sample from a tissue specimen processed according to the present invention, and lane 7 contains control RNA.

DETAILED DESCRIPTION OF THE INVENTION

Figure 3:
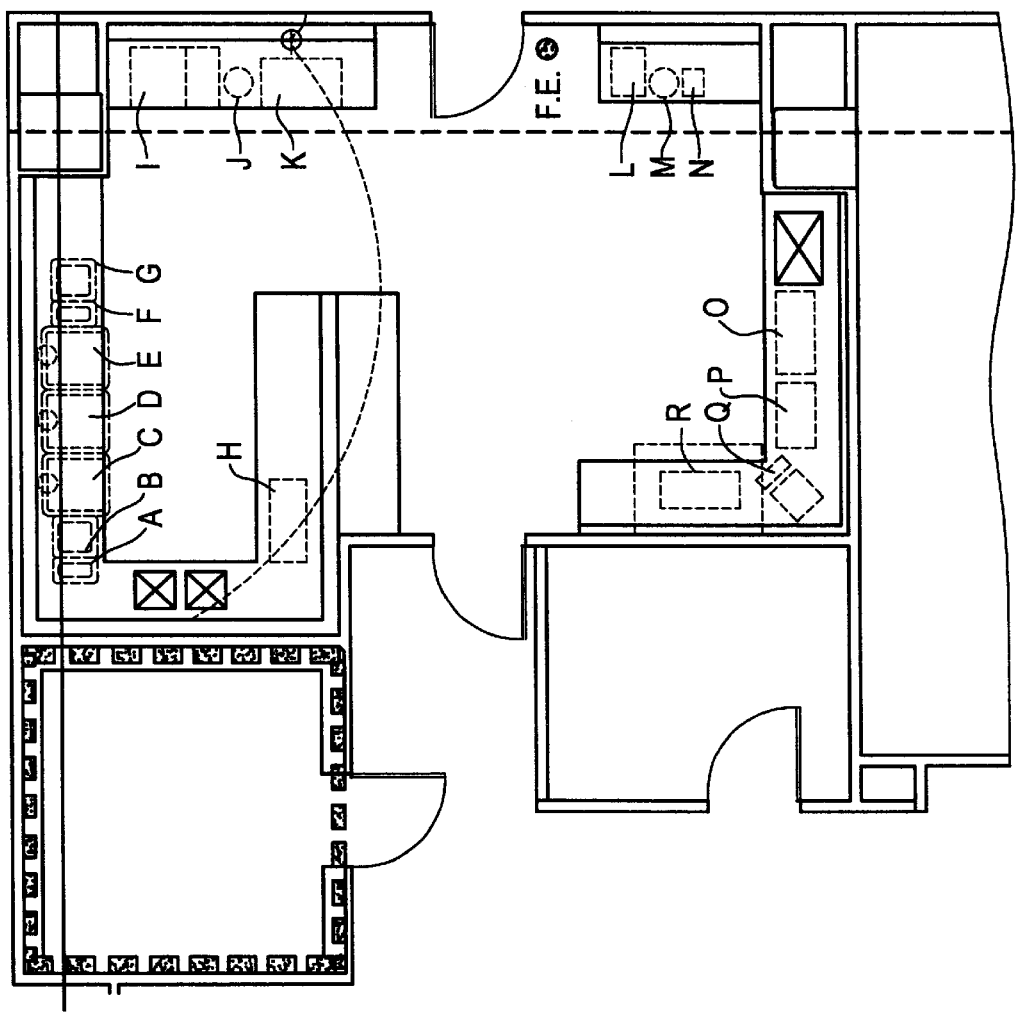
FIG. 3 is a schematic plan view of a tissue processing facility provided in accordance with the invention.

A process and apparatus for rapid, continuous histological processing of tissues is disclosed. The steps of fixation, dehydration, fat removal, and impregnation can be performed in less than about two hours; this allows a pathologist to evaluate samples shortly after receipt, perhaps while the patient is still in the operating or recovery room. Patient anxiety can be reduced by reducing the time required for pathological diagnosis. Rapid and continuous processing is accomplished by decreasing the thickness of tissue specimens, use of non-aqueous solutions composed of admixtures, solution exchange at elevated temperature and with agitation, uniform heating of tissues and solutions with microwave radiation, impregnation under vacuum pressure, or a combination thereof.

Fixation, dehydration, and removal of fat are required for the preparation of tissue prior to impregnation. These steps are facilitated by trimming the tissue to a suitable size prior to processing, and using cassettes which hold such tissue blocks and allow their easy transfer between solutions for fixation, dehydration, removing fat, and impregnation.

Fixation initiates hardening of the tissue specimen, and may preserve cell morphology by cross linking proteins and halting cellular degradation. Without chemical fixation, endogenous enzymes will catabolize and lyse the cell, and the tissue microanatomy will be altered. Such fixatives may be a ketone, aldehyde, alcohol, acetic acid, heavy metals, chromic acid, picric acid, or osmium tetroxide. Indications that fixation was inadequate can include: disassociation of tissue structures, bubbles in tissue sections, poor and irregular staining, shrunken cells, clumping of cytoplasm, condensation and less distinct nuclear chromatin, and autolysis/hemolysis of erythrocytes.

Dehydration removes water from the tissue specimen to promote hardening. Replacement of water in the tissue specimen with a dehydrating agent also facilitates subsequent replacement of the dehydrating agent with material used for impregnation. This solution exchange is enhanced by using a volatile solvent for dehydration. The dehydrating agent may be low molecular weight alcohols, ketones, dioxane, alkylene glycols, or polyalkylene glycols. Failure to dehydrate the specimen can lead to inadequate impregnation, poor ribbon formation during sectioning, clefts in tissue sections, dissociation of structures, water crystals in tissue sections, and poor staining.

Fat in the tissue specimen is removed with a solvent because fat impairs clearing and impregnation. Inadequate fat removal can result in spreading artifacts of tissue sections, wrinkling of tissue sections, and poor staining.

Optionally, the tissue specimen is cleared. The clearant extracts dehydrating agent from the tissue specimen and reduces its opacity. Examples of clearants include xylene, limonene, benzene, toluene, chloroform, petroleum ether, carbon bisulfide, carbon tetrachloride, dioxane, clove oil, or cedar oil.

Finally, once the tissue specimen is suitably fixed and dehydrated, it is hardened by impregnation with an agent such as wax, celloidin, polyalkylene glycols, polyvinyl alcohols, agar, gelatin, nitrocelluloses, methacrylate resins, epoxy resins, or other plastics. Appropriate hardening of the tissue specimen with adequate preservation of cellular morphology is required prior to placing the impregnated specimen in a block and obtaining ten micron or thinner sections with a microtome knife. Preferred impregnation materials are commercial wax formulae, mixtures of waxes of different melting points (e.g., liquid mineral oil and solid paraffin), paraplast, bioloid, embedol, plastics and the like. Paraffin has been chosen for use in the examples herein because it is inexpensive, easy to handle, and ribbon sectioning is facilitated by the coherence of structures provided by this material.

If processing of the tissue specimen is incomplete, the sections cut by the microtome knife will appear cracked or "exploded". Tissue processing is deemed a failure when one or more of the following problems is encountered: embedded tissue blocks are too soft or too hard, sections fall out or show an amount of compression different from the embedding agent, sections appear mushy, tissue ribbons fail to form or are crooked, sections crumble or tear, erythrocytes are lysed, or clumping of cytoplasm, condensation of chromatin, basophilic staining of nucleoli, shrunken cells, spreading artifacts and moth-eaten effect.

For wax-impregnated sections on glass slides, the wax may be melted and removed prior to staining or immunohistochemistry. The tissue section is rehydrated and then analyzed as described below with stains or antibodies. After staining is completed or the histochemical reaction is developed, the slide may be coverslipped and viewed under a microscope. Alternatively, the stained or antibody-decorated specimen may be studied with an instrument for cytometry. The tissue blocks may be stored for archival purposes or retrospective studies.

The present invention is compatible with preparation of nucleic acids, DNA or RNA, from processed tissues. Thus, genetic study is possible for specimens collected routinely in the clinical pathology laboratory. The combined power of these technologies will be great. Histological observations may be correlated with genetics by analyzing one section by staining or immunohistochemistry, and preparing nucleic acids from an adjacent section for genetic analysis. For example, diseased and normal regions of the same section may be compared to detect genetic differences (e.g., mutations, levels of transcription), disease progression may be characterized by comparing genetics differences in samples taken at several time points, and tumor evolution may be assessed by following the accumulation of genetic differences from primary cancer to metastasis.

Many features distinguish the present invention: (a) thin slicing of the tissues prior to processing; (b) continuous input of tissue specimens, and continuous flow through the system; (c) elimination of water from solutions (i.e., non-aqueous solutions); (d) fixation, dehydration, fat removal, clearing, and impregnation of tissue performed with uniform heating (e.g., microwave energy); (e) admixture solutions to fix-dehydrate-remove fat, fix-dehydrate-remove fat-clear, and clear-impregnate; and (f) impregnation of tissue under reduced pressure with degassed impregnating agent. These features make the present invention simple, practical, easy to implement, and amenable to automation.

Hematoxylin-eosin staining is commonly used for histological study and may be considered a standard for comparison by pathologists. In addition, the present invention has been found to be compatible with other stains including trichrome, reticulin, mucicarmine, and elastic stains as described in general references such as Thompson (*Selected Histochemical and Histopathological Methods,* C. C. Thomas, Springfield, Ill., 1966), Sheehan and Hrapchak (*Theory and Practice of Histotechnology,* C. V. Mosby, St. Louis, Mo., 1973), and Bancroft and Stevens (*Theory and Practice of Histological Techniques,* Churchill Livingstone, New York, N.Y., 1982). Such staining procedures would take between 30 minutes and several hours to complete, although rapid staining procedures are available from Fisher Scientific that require only five minutes to accomplish.

Tissue may be obtained from an autopsy, a biopsy (e.g., endoscopic biopsy), or from surgery. For cancer surgery, the ability to provide a pathological diagnosis from a stained tissue section will provide the surgeon with information that may be used prior to the patient's departure from the operating room. For example, an indication from the pathologist that the cancer is confined to the resected tissue may allow the surgeon to be conservative in treatment and to preserve neighboring healthy tissue. Alternatively, a finding by the pathologist that cancer is not confined to a resected organ would permit more aggressive surgical treatment while the patient was still in the operating room.

Over 20,000 samples of tissue have been successfully processed by the present invention, including: brain, breast, carcinoma (e.g., bowel, nasopharynx, breast, lung, stomach), cartilage, heart, kidney, liver, lymphoma, meningioma, placenta, prostate, thymus, tonsil, umbilical cord, and uterus. Mineralized tissue (e.g., bone, teeth) would require decalcification prior to processing by the present invention. For example, tissue may be decalcified with a hydrochloric acid/ethylenediaminetetraacetic acid (EDTA) solution from Stephens Scientific (Allegiance Healthcare Supply, catalog no. 1209-1A) according to the manufacturer's instructions.

Tissue sections processed by the present invention may also be used in immunohistochemistry. The present invention provides tissue specimens in which antigen is recovered and preserved, the choice of fixative may be optimized for recovery and preservation of particular antigens. Non-specific binding sites are blocked, antigen is bound by specific antibody (i.e., the primary antibody), and non-bound antibody is removed. If labeled with a probe or signal generating moiety, the primary antibody may be detected directly but it is preferred to attach the probe to a protein (e.g., a secondary antibody) that specifically binds the primary antibody. Secondary antibody may be raised against the heavy or light chain constant region of the primary antibody. This amplifies the signal generated by an antigen-antibody conjugate because each primary antibody will bind many secondary antibodies. Alternatively, amplification may occur through other specific interactions such as biotin-streptavidin. Antibody binding is performed in a small volume to reduce usage of expensive reagents and maintain a high binding rate; evaporation of this small volume is reduced by incubation in a humidity chamber. The signal generating moiety is preferably an enzyme which is not otherwise present in the tissue. For example, alkaline phosphatase and horseradish peroxidase may be attached to the secondary antibody or conjugated to streptavidin. Substrates are available for these enzymes that generate a chromogenic, fluorescent, or luminescent product that can be detected visually.

The staining pattern for antigen may be used to localize expression of the antigen in the context of cellular structures revealed by counterstaining. Antigen expression can identify cell or tissue type, developmental stage, tumor prognostic markers, degenerative metabolic processes, or infection by a pathogen.

Antigen-antibody binding may also be visualized with radioactive, fluorescence, or colloidal metal probes by autoradiography, epifluorescent microscopy, or electron microscopy, respectively. Similar probes may be used to detect nucleic acid in the tissue section by in situ hybridization to identify genetic mutations or transcripts; alternatively, the nucleic acid (DNA or RNA) may be extracted from tissue sections and analyzed directly by blotting, or amplified prior to further genetic analysis.

Mutations may be germline and used to trace genetic predisposition of disease, or mutations may be somatic and used to determine genetic alterations in disease pathogenesis. The disease may be a metabolic or neurologic disorder, malignancy, developmental defect, or caused by an infectious agent. The present invention preserves material for genetic analysis by a simple procedure and room temperature storage.

It is envisioned that the present invention will preserve tissue that yield greater amounts of nucleic acid with a higher average molecular weight than tissues processed by conventional processes.

In accordance with an exemplary system for tissue processing provided in accordance with the present invention, a series of tissue processing stations may be provided, e.g., in a single tissue processing unit or area. By way of non-limiting example, a suitable tissue processing facility is illustrated in FIG. 3.

The first step in the process, which may be carried out at the tissue processing facility or elsewhere, is to prepare a suitable tissue sample for hardening and ultimate examination. Typically, a slice of the tissue of interest is prepared. The finest slice possible is obtained, of about 1 to 3 mm and preferably 1 to 2 mm in thickness. Processing time is proportional to the size of the tissue sample being processed. The tissue slice is placed in a tissue cassette in which the tissue is contained during the immediately following processing steps. The tissue cassette is next placed in a first solution provided in accordance with the present invention.

Figure 4:
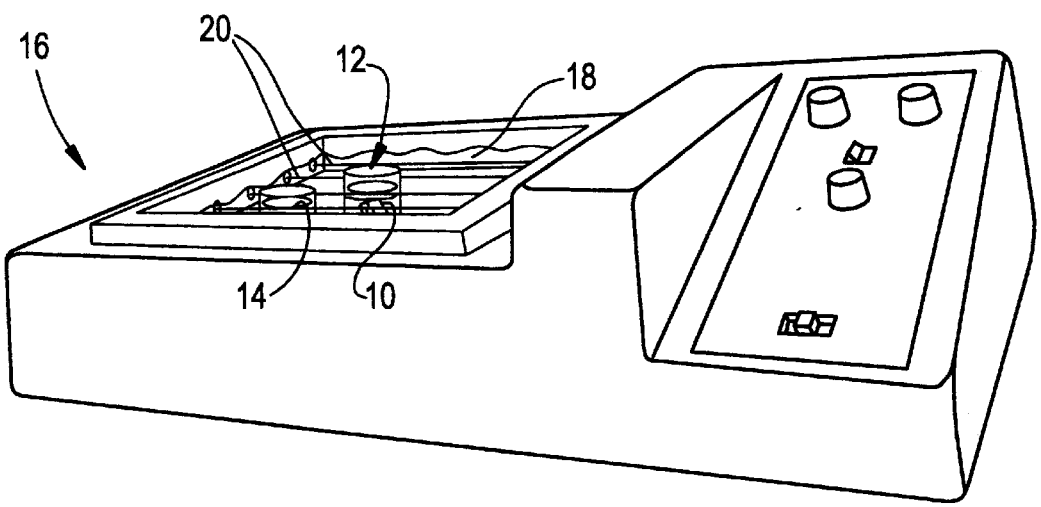
FIG. 4 shows an exemplary shaker bath provided as a part of the apparatus and system of the invention.

By way of example, the cassette 10 may be placed in a conventional beaker 12, having the first solution 14 therein, preferably by itself as the process described is a substantially continuous one, or together with a limited number of other, similar tissue cassettes. The beaker 12 is then placed in a shaker bath 16, as illustrated in FIG. 4, for gently agitating and heating the same. We have used a LAB-LINE/ DUBNOFF incubator-shaker bath for this purpose. Rather than water, as it is our goal to minimize moisture to which the tissue samples are exposed and, in fact, ultimately to dehydrate the same, we have provided glycerine as the temperature conducting fluid 18 in the shaker bath 16. Glycerine has the advantage that it is an effective conductor of thermal energy but it does not evaporate. Evaporation would undesirably increase the moisture of the environment in which the tissue is processed, and would require periodic replenishment. Because the glycerine neither needs replacement nor adds moisture to the environment, it is most preferred. For this stage of the process, the tissue sample (in cassette 10) is disposed in the first solution, in the shaker bath 18 for approximately 3–15 minutes.

Supplemental agitation is desirably also provided during the shaker-bath step. Presently, an external pump (A) (FIG. 3) is provided with a tube (not shown) therefrom inserted into the solution beaker 12 or other receptacle for bubbling and thus agitating its contents. An aeration diffusion nozzle or plate may be provided to provide for more uniform solution agitation as deemed necessary or desirable.

To ensure that the tissue cassette 10 and first solution containing beakers 12 remain upright and in a desired disposition, we have modified the conventional shaker-bath to provide transverse wires or stays 20, e.g., four wires, defining, e.g., five longitudinal channels in which tissue cassette containing beakers 12 may be disposed. Thus, for example, sample containing beakers 12 may be regularly added to the shaker-bath 18 and sufficiently processed tissue samples removed in turn therefrom for further processing as described hereinbelow, by adding new samples on the left end of the shaker bath and removing sufficiently processed samples from the right end thereof.

Next the tissue sample cassette 10 is exposed to a series of fluids while simultaneously being agitated and subjected to microwave radiation. In the currently proposed embodiment, three microwave units are provided, as shown in FIG. 3, each having a different solution in which the tissue sample containing cassette is submerged for a prescribed period. In the alternative, a single source of microwave energy could be provided. However, such would require sequential placement of the respective solutions for receiving the tissue cassette. While for a single tissue sample such solution placement and replacement would not significantly increase the duration of the tissue processing cycle, it can be appreciated that the use of a single microwave that receives multiple solutions, may hinder the continuity of the process with respect to subsequent samples. Indeed, where a series of microwave units are provided, as a given tissue sample is moved from one microwave to the next having the next solution, a subsequent tissue sample can then be received in the first microwave unit. Thus, providing a unit for each of the respective solutions means that a subsequent tissue sample need not be held while all microwave processing steps of the proceeding sample have been completed. It is to be understood, however, that with the noted hindrance of continuity, the three microwave units illustrated could be reduced to two or even one. Likewise, other steps in the process may be combined or sub-combined as deemed necessary or desirable from a balance of process continuity versus a potential reduction in manpower, equipment, space requirements, etc. An exemplary such more compact unit is discussed in greater detail below, with reference to FIG. 7.

Figure 5:
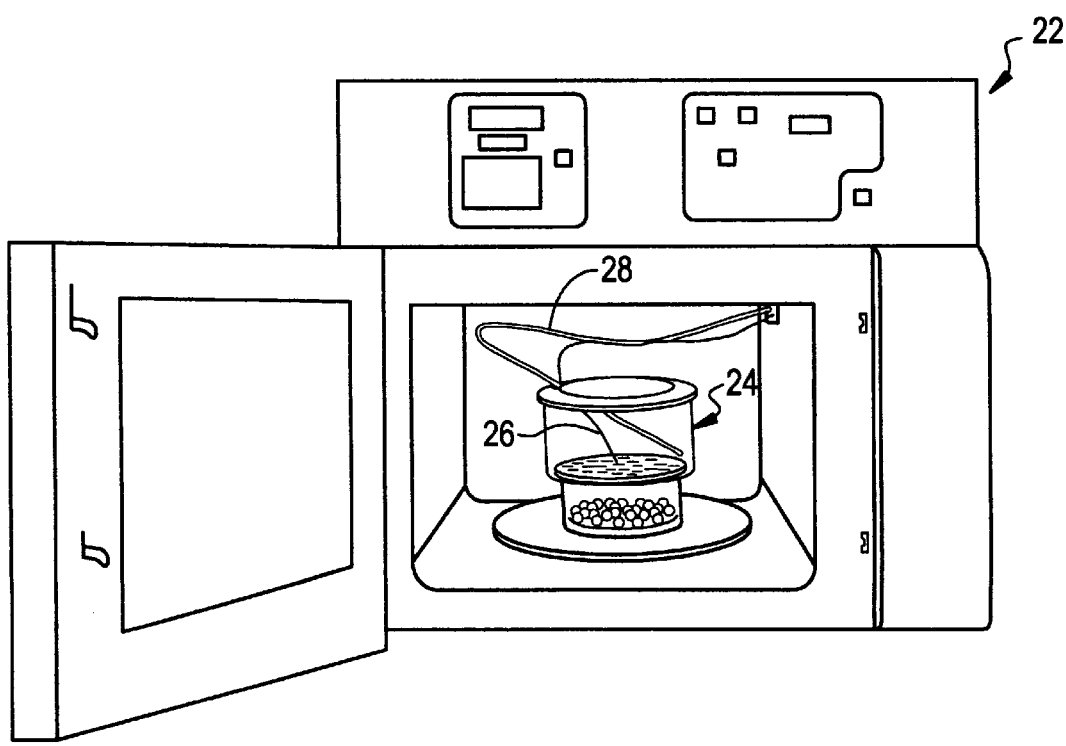
FIG. 5 shows an exemplary microwave oven for use as a part of the apparatus and system of the invention.

With reference now to FIG. 5, an exemplary microwave unit 22 for tissue processing is illustrated. For applying microwave radiation, we are currently using laboratory microwave ovens obtained from Energy Beam Sciences, Inc. We have used two microwave processor models, H-2800 and H-2500. Either model or another, similar such system could be used. By way of example, a Pyrex or other clear microwaveable fluid receptacle 24 is utilized to hold respectively second, third and fourth solutions provided in accordance with the invention in each of the three microwave units (FIG. 3). A temperature probe 26 is placed in the solution to ensure that the temperature of the respective bath is within the desired range. Moreover, to provide for agitation, which accelerates the tissue processing, aeration is provided. The microwave units we have used include a tube 28 for aeration. A single tube may be inserted into the bath, but for more uniform and complete agitation, it is most preferred to provide a diffusion plate or nozzle head (not shown in detail) in cooperation with the gas tube 28 for diffusing the agitating bubbles, e.g., across a substantial portion of the diameter of the solution receptacle for uniform agitation of the entire volume of solution. Such diffusion plates and nozzles are well known and can be provided, e.g., at the base of the solution receptacle.

Conventionally, paraffin is degassed as a part of the tissue processing procedure. Degassing removes organic solvents from the paraffin. To enhance this process, and to reuse the paraffin in the system we propose continuous degassing. This is accomplished by maintaining the vacuum within the covered Pyrex 32 at 640 mm. Hg.

Figure 6:
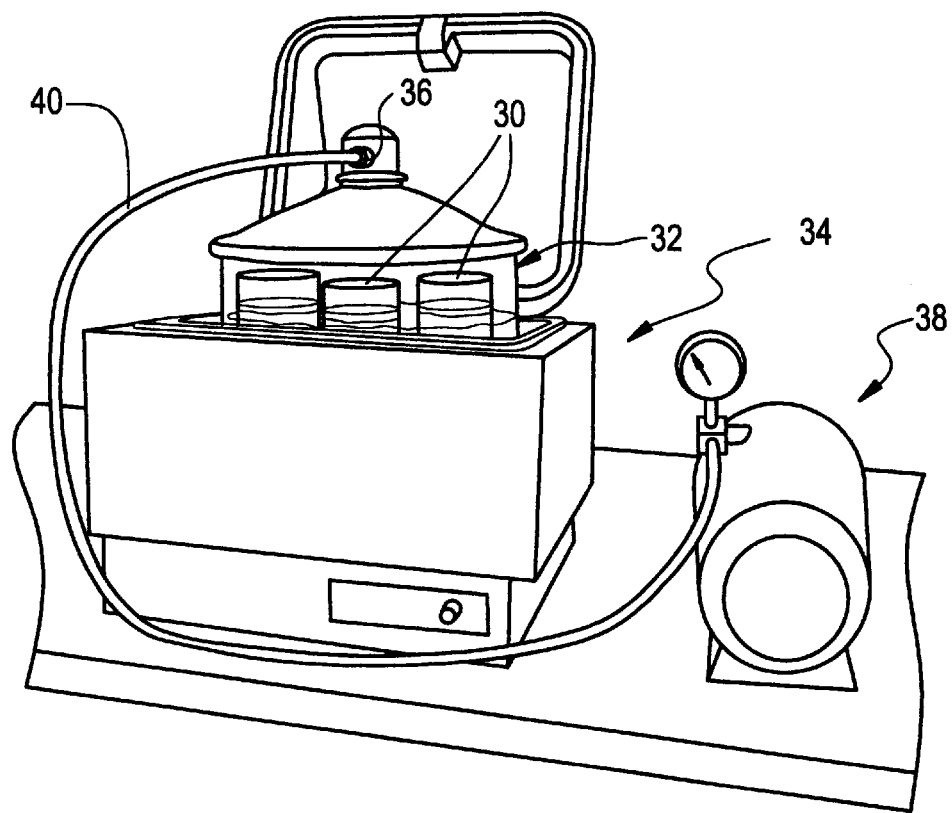
FIG. 6 shows an exemplary paraffin bath provided as a part of the apparatus and system of the invention.

Following the three sequential steps employing microwave radiation, the tissue sample cassette(s) are placed in a paraffin bath, as shown in FIG. 6. Currently, we provide a paraffin bath comprising three paraffin bath stations (beakers) 30 provided within a covered Pyrex jar 32. For the purpose of temperature control, the Pyrex jar 32 is placed in, e.g., a Poly Science brand water bath 34. By applying a grease or the like to the internal edges of the flanges on both the lid and jar, an airtight coupling can be provided between the lid and jar and thus a vacuum can be pulled through a tooled hose connector 36 provided in the lid. Suitable such Pyrex brand jars are available from Fisher Scientific. We have used Model No.01-092-25. To create a vacuum within the Pyrex jar 32, a conventional pressure/vacuum pump 38 is coupled to a tube 40 that is in turn coupled to connector 36. A suitable such power operated pump is available from Fisher Scientific and has for example a 100 psi max. Agitation is preferably provided during the paraffin bath step, either through vibratory agitation, ultrasound, or potentially via aeration.

Next the tissue sample must be embedded. For that purpose we use a conventional Tissue-Tek embedding console system (I) (FIG. 3) available from Miles/Sakura, e.g. Model No. 4708.

The embedded tissue sample is then cut in a conventional manner with a microtome (L) (FIG. 3) and floated (M) for placement, we use the Leitz 1512 Microtome, and the Lipshaw Electric Tissue Float Model 375.

After the slice is disposed on the slide, the slide is heated to remove the paraffin. We have used the Isotemp Oven 300 series available from Fisher (K) (FIG. 3).

Next the slides are stained. To accelerate the staining process, we propose to use an automated stainer (O) (FIG. 3) to reduce the number of personnel and time required. A non-continuous process could use the Sakura diversified stainer DRS-601 which stains slides in batches; alternatively, a continuous process could use a Leica auto stainer XL which contains a dewaxing stage so that separate incubation in an oven may be omitted. The fixed and stained tissue sample is then covered, e.g. with the Tissue-Tek coverslipper, Manufacturer No. 4764 (R) (FIG. 3).

As described above, the system for carrying out the dehydration and impregnation in accordance with the invention can be a series of discrete units. In the alternative, as also noted above, one or more steps can be carried out in a single processing component or unit. As also discussed above, the number of units provided and the steps carried out by each unit impacts the continuity of the processing unit. Thus, in low volume environments, a single unit for carrying out a plurality of the tissue processing steps may be advantageous and will not significantly impact continuity of tissue processing. In higher volume systems environments, two or more units may be preferred.

Figure 7:
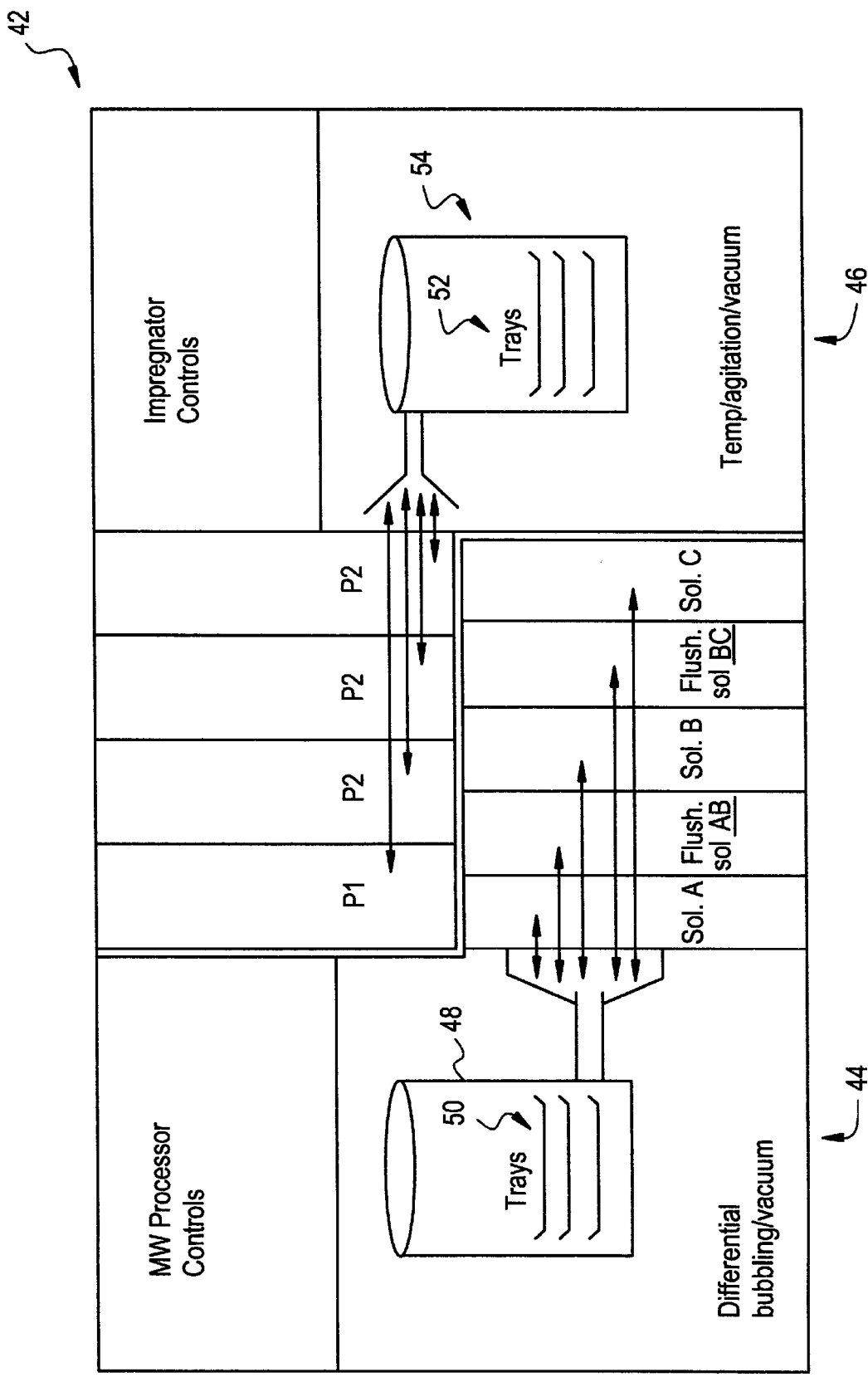
FIG. 7 is a schematic illustration of a microwave/impregnation unit provided in accordance with an alternative embodiment of the invention.

An exemplary combined unit 42 is illustrated in FIG. 7. The combined unit 42 in fact includes two subunits; a microwave processor unit 44 and an impregnator unit 46. The microwave processor unit 44 is provided for sequentially submerging the tissue being processed in solution A, solution B, and solution C, in each instance agitating the solution and exposing the tissue to microwave energy. Thus, in the illustrated embodiment, a vessel 48 is provided for receiving for example one or more trays 50 on which one or more tissue cassettes 10 may be placed. The vessel 48 is fluidly coupled to a source of each of the solutions for tissue dehydration. Thus, once the tissue cassette(s) are placed on the respective tray(s) 50, solution A is conducted to the vessel 48 and microwave energy is applied thereto simultaneous to agitation via, for example, an aeration tube (not shown in FIG. 7). After a sufficient time of exposure has passed, solution A is drained and the tissue cassettes are preferably flushed either with solution B or with a combination of solution A and solution B so as to substantially eliminate residual solution A. Solution B is then fed to the vessel 48 whereupon microwave energy and agitation are again applied for a prescribed period. At the conclusion of administration of solution B, solution B is returned to a storage vessel therefor and the tissue samples are flushed either with solution C or a combination of solution B and solution C. Thereafter, solution C is fed to the vessel 48, agitation and microwave energy are applied, and ultimately solution C is drained. The tissue samples are then ready for impregnation.

In the illustrated embodiment impregnation is carried out in a second subunit 46 of the assembly. This allows impregnation to be carried out while a subsequent tissue sample(s) are subject to microwave energy application. If a single unit is provided, then the vessel used for microwave processing can be used for impregnation however the microwave energy would not be applied thereto during the impregnation steps.

In accordance with the proposed impregnation process, a series of paraffin solutions, e.g., 3 or 4, are applied to the tissue cassettes disposed e.g. on suitable trays 52 in a vessel 54, to provide sequential paraffin baths to effect the impregnation of the tissue sample as a final step in the tissue preparation process. In the impregnator subunit 46, the tissue samples are placed under a vacuum at a controlled elevated temperature. The tissue samples are preferably also agitated during this step with a magnetic stirrer, ultrasound, or air bubbler.

The remaining embedding, etc. steps of slide preparation are carried as outlined above with reference to FIG. 3.

In accordance with the invention, additional, specialized instruments and apparatus have been developed to facilitate tissue processing in general and in accordance with the invention, in particular. These specially designed instruments and apparatus are described herein below.

Figure 8:
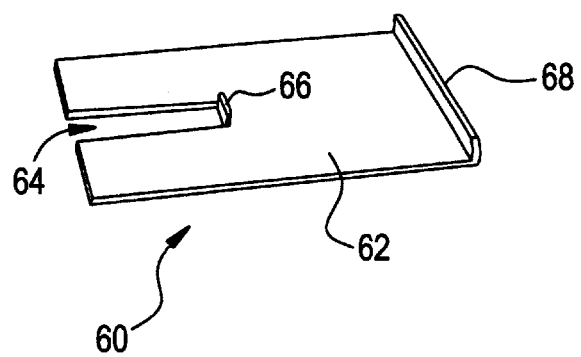
FIG. 8 is a schematic illustration of a slicing guide provided in accordance with an exemplary embodiment of the invention.

As noted above, it is difficult to cut a thin slice of a solid tissue sample. On the other hand it is desirable, in terms of minimizing dehydration and fixation time, to have the tissue sliced as thinly as possible in advance of the dehydration process. To facilitate creation of a thin slice we have proposed three instruments to aid the pathologist. One, for convenience referred to herein as a slicing guide 60, as illustrated in FIG. 8, is in the form of a thin metal plate 62 on the order of, e.g., 1 to 2 mm in thickness, having a cutout 64 the width of, for example, a thumb nail (about 1 cm$^2$). A stop 66 is defined at the end of the cutout or notch 64 to serve as a knife or blade stop. To facilitate picking up the slicing guide 60 from a flat surface or other cutting surface, a lip 68 may be provided at the end of the metal plate 62, remote from the cutting notch. To provide a thin slice of tissue, a larger segment of tissue is placed over the cutout or notch 64 so that a portion thereof is disposed in the notch. Pressure is then applied to the exposed surface of the tissue and a cutting instrument is placed against and slid horizontally along the slicing guide plate so as to sever the tissue disposed in the notch 64 from the remainder of the tissue. Engagement of the cutting blade with the blade stop 66 completes the cutting process and the bulk of the tissue, disposed above the cut, is placed aside. The remaining tissue, disposed in the slot, can then be placed in a suitable tissue cassette for dehydration and impregnation.

As can be appreciated, the slicing guide 60 facilitates the production of a thin slice of tissue of generally uniform thickness which may be further processed.

Figure 9:
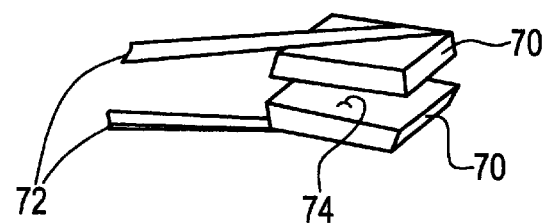
FIG. 9 is a broken away view of a tissue clamp and slicing assembly provided in accordance with another embodiment of the invention.

As another alternative for producing a thin tissue slice, we have proposed to provide flat plates or blocks 70 at the end of an otherwise conventional forceps 72, as schematically illustrated in FIG. 9. The blocks may be permanently or temporarily secured to the ends of the forceps. This provides rather large, flat clamping surfaces 74. The tissue to be cut may be placed between the clamping blocks 70 and a sharp blade passed between the clamping blocks to slice the tissue. By cutting closely to one of the two generally planar flat surfaces 74, a thin tissue slice of generally uniform thickness can be provided. The parallel rather large flat surfaces provide uniform pressure distribution thus holding the tissue in position during the cutting process and then ensuring a uniform cut that preferably preserves the integrity of the tissue.

Figure 10:
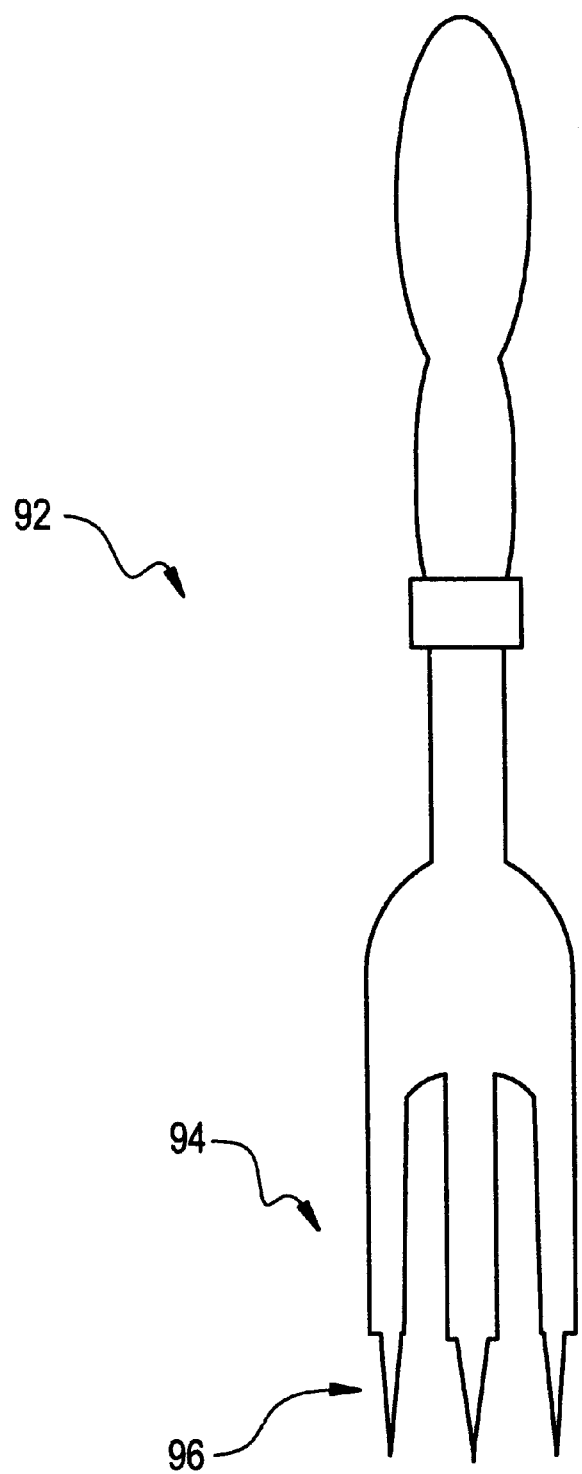
FIG. 10 is a schematic illustration of a tissue holder provided in accordance with a further embodiment of the invention.

To hold the tissue in position during cutting we have also proposed a three prong fork-like instrument 92, illustrated in FIG. 10. In the illustrated embodiment the prongs 94 are spaced from each other by approximately one centimeter and each has a sharp, pointed tip 96 to facilitate penetration of the tissue with minimal disruption. By holding the tissue to a cutting board with the prongs 94 of the instrument 92, suitable slices of tissue can be obtained by cutting parallel to or between the prongs. In the illustrated embodiment, the instrument 92 is characterized in that the prongs have a length on the order of 5–10 centimeters to accommodate a variety of specimens and a handle of about 8 centimeters in length, itself spaced from the prongs by 2–4 centimeters, to facilitate manipulation of the instrument and a sure grip during cutting. We have found that the fork-like instrument 92 is particularly advantageous in obtaining sections from organs such as the intestine and gallbladder. Indeed, securing such specimens with prongs 94 prevents the various layers of tissue from sliding upon each other during the cutting process.

Figure 11:
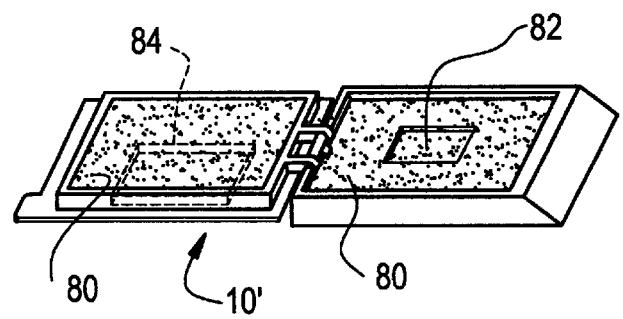
FIG. 11 is a schematic illustration of a tissue cassette provided in accordance with the invention for receiving small tissue samples.
Figure 12:
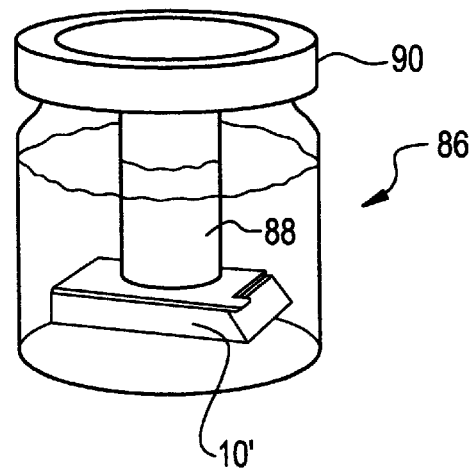
FIG. 12 shows a tissue receiving and transporting jar with tissue cassette in accordance with an embodiment of the invention.

We have also proposed to provide a tissue receiving unit and cassette for use in the operating room, to facilitate transport of tissue, particularly very small segments of tissue, for example those obtained by needle biopsy. When such biopsied tissue is put directly into, for example, a jar of suitable solution, it can often be difficult for the lab technician to retrieve the minute tissue sample from the jar and in particular to ensure that all biopsied tissue is retrieved. Thus, as illustrated in FIGS. 11 and 12, we have proposed to provide tissue cassettes 10' to the operating room for immediately receiving such minute tissue samples.

To contain such tissue samples within the tissue cassette 10', we have provided thin sheets of biopsy sponge material 80, which is an open cell plastic foam, at least one of which has a partial depth recess 82 defined therein to provide, together with the other biopsy sponge a compartment for receiving the biopsied tissue. Thus, in the operating room the biopsied tissue can be disposed immediately in the recessed portion 82 of one of the biopsy sponges 80 and the tissue cassette 10' closed. To maintain the integrity of the tissue for transport to the processing lab, the tissue cassette 10' is placed within a jar of suitable solution. To facilitate retrieval of the cassette and to ensure that it is maintained fully submerged in the solution, we have provided a specimen jar 86 having a columnar support 88 projecting from the lid 90 and having structure at the tip thereof 90 for coupling to complementary structure 84 on the tissue cassette 10'. FIG. 12 shows the tissue cassette 10' attached by its top surface. However, alternative attachment points are possible such as the bottom surface or the hinged side of the cassette. Furthermore, two or more cassettes may be attached to the columnar support 88.

Thus the tissue cassette 10' with the biopsied tissue therewithin can be temporarily secured to the distal end of the columnar support 88 and inserted into a suitable solution for transport. At the tissue processing lab, the lid 90 is removed from the jar 86 and the tissue cassette 10' removed from the column 88. Any suitable fasteners such as velcro type fasteners, plastic snap lock, dove tail slide connectors or other cooperative engagement structure can be provided to attach the tissue cassette 10' to the support column 88. The solution within the specimen jar 86 may be a transport (aqueous) solution or the first (non-aqueous) solution. It would be convenient to provide the specimen jar in the operating room with the cassette attached to the outside of the jar and then to invert the lid so that the cassette is immersed in the solution within the jar after tissue is placed within the cassette.

The present invention will have many advantages over conventional methods in the areas of the practice of pathology, patient care, biomedical research, and education.

The availability of microscopic diagnosis of tissue samples within about 40 minutes to about 2 hours after receipt will allow rapid, or even real-time, clinical interaction between surgical intervention and pathological evaluation. This may bring about significant improvements in patient care by eliminating or reducing to a minimum patient anxiety during the wait for diagnosis of disease, prognosis, and planning for treatment.

Consequently, there will be a drastic reordering of the workflow in pathology laboratories. Clinical laboratory space, pathological expertise, and clerical and technical personnel will be utilized more efficiently. Continuous workflow will improve accessibility and responsiveness of pathologists who process and evaluate specimens, reduce the number of pathologists needed to process and evaluate specimens, and may also improve medical education, particularly the accessibility and responsiveness of residency programs.

The smaller volume of reagents will result in cost savings. Elimination of formaldehyde and xylene and the diminished requirement for other hazardous chemicals will provide benefits to the environment and increased safety in the laboratory.

Standardization of tissue fixation and processing procedures will ease comparison of specimens from different laboratories. Artifacts in histology due to the use of formaldehyde and/or prolonged processing will be eliminated; thus, allowing more precise evaluation of microscopic morphology of normal and diseased tissues. Similarly, antigen retrieval and staining will be improved. For genetic analysis, formaldehyde-induced DNA mutations will be eliminated and extraction of nucleic acid from archival material may be enhanced. The feasibility of RNA studies from stored, fixed paraffin-embedded tissue opens unlimited avenues for diagnostic and research applications.

All books, articles, applications, and patents cited in this specification are incorporated herein by reference in their entirety.

The following examples are meant to be illustrative of the present invention; however, the practice of the invention is not limited or restricted in any way by them.

EXAMPLES

Example 1

Two mm thick or thinner slices of fresh or previously fixed tissue were held in tissue cassettes and placed in a non-aqueous first solution of:

40% isopropyl alcohol,

40% acetone,

20% polyethylene glycol (average molecular weight 300), and

1% dimethyl sulfoxide (DMSO) (i.e., 10 ml per liter of the above mixture).

Tissues samples were incubated for 15 min at a glycerin bath temperature between 45° C. and 50° C. The 400 ml solution for fixation was placed in a 500 ml beaker in a water bath shaker (linear displacement of 5 cm/sec). Additional agitation of the fixation solution was provided by bubbling with an air pump.

Fixation, dehydration, fat removal, clearing, and impregnation are accomplished by sequential exposure of the tissue specimen to three different solutions (the second, third and fourth solutions described above), one in each of three microwave ovens from Energy Beam Sciences. A one liter solution of 70% isopropyl alcohol and 30% polyethylene glycol (average molecular weight 300) is placed in the first oven (model H2800) in a 1500 ml beaker, the solution in the second oven (model H2800) consists of one liter of 70% isopropyl alcohol and 30% xylene in a 1500 ml beaker, and the third oven (model H2500) contains a solution of 1000 ml of xylene and 300 gm of paraffin in a 1500 ml beaker. Ten ml of DMSO per liter are added to these three solutions. Heating at 60° C. by microwave radiation is effected for 15 minutes in the first oven, and 5 minutes each in the second and third ovens (75% power setting with a cycle of 2 seconds).

To continue paraffin impregnation after completion of the microwave radiation steps, tissue sections were incubated in four 500 ml baths of molten paraffin placed within a large dessicator filled with paraffin, and resting in a glycerin bath at 75° C. Tissue sections were transferred from one paraffin bath to the next at 3 minute intervals, for a total impregnation time of 12 minutes. Each 3 minute interval was measured from the time that the pressure reading is about 640 mm. Of Hg. No agitation was used during this step.

Example 2

Fixation, dehydration, fat removal, and paraffin impregnation of fresh or fixed tissue sections, approximately 1 mm thick, was accomplished in 40 minutes by exposing these tissue sections to four successive steps as follows.

Step 1.

In this example, the first solution consisted of:

60% isopropyl alcohol,

10% acetone,

30% polyethylene glycol (average molecular weight 300), and dimethyl sulfoxide (DMSO) added at an approximate concentration of 1% of the total volume. One liter of this solution suffices to fix 60 samples of tissue held in tissue cassettes. The samples were incubated at 55° C. in a commercial tissue microwave processor (H2500 or H2800, Energy Beam Sciences) for 5 min each in a series of three baths containing the first solution (15 min total incubation); agitation of the solution was obtained by bubbling to accelerate solution exchange.

Step 2.

The samples were incubated in a solution of 70% isopropyl alcohol, 30% acetone, and DMSO added at an approximate concentration of 1% at 60° C. Samples were heated in a commercial tissue microwave processor (H2800, Energy Beam Sciences) for 5 min each in two beakers containing the solution (10 min total incubation), which were agitated by bubbling.

Step 3.

Following microwave irradiation, impregnation was initiated by incubation in a wax solution of 25% mineral oil and 75% molten paraffin placed in a large dessicator resting in a 60° C. or 70° C. glycerin bath, under a vacuum of about 200 mm of Hg, for 5 min. Paraffin was degassed prior to use as described in Example 1.

Step 4.

Impregnation was completed by incubation in four baths of molten paraffin placed within a large dessicator resting in a glycerin bath at 75° C. Tissue sections were transferred from one paraffin bath to the next at 3 min intervals, for a total impregnation time of 12 min. Each 3 min interval was measured for the time that the pressure reading is about 640 mm of Hg.

In this example, 6 ml of a color indicator stock solution (10 $\mu$m methylene blue in 1000 ml of isopropyl alcohol) was added to each of the solutions of isopropyl alcohol and acetone. Tissue specimens acquire a blue tint that facilitates their handling during impregnation and handling; penetration of the tissue specimen may also be monitored by observation of an even blue color throughout the tissue specimen.

Example 3

Fixation, dehydration, fat removal, and paraffin impregnation of fresh or fixed tissue sections, up to about 1 to 2 mm thick, may be accomplished in 65 minutes as follows.

Step 1.

In this example, the first solution consists of:
  40% isopropyl alcohol,
  40% acetone,
  20% polyethylene glycol (average molecular weight 300),
  glacial acetic acid added at an approximate concentration of 0.5% of the total volume, and
  dimethyl sulfoxide (DMSO) added at an approximate concentration of 1% of the total volume. One liter of this solution suffices to fix 60 samples of tissue held in tissue cassettes. The samples are incubated at 65° C. in a commercial tissue microwave processor (H2500 or H2800, Energy Beam Sciences) for 15 min in a 1500 ml beaker containing the first solution; agitation of the solution is obtained by bubbling to accelerate solution exchange.

Step 2.

The samples are incubated in a solution of 55% isopropyl alcohol, 25% acetone, 10% polyethylene glycol (average molecular weight 300), 10% low viscosity mineral oil, glacial acetic acid added at an approximate concentration of 0.5% of the total volume, and DMSO added at an approximate concentration of 1%. Samples are heated at 65° C. in a commercial tissue microwave processor (H2800, Energy Beam Sciences) for 15 min in a 1500 ml beaker containing the solution, which is agitated by bubbling.

Step 3.

The samples are incubated in a solution of 55% isopropylic alcohol, 25% acetone 20% low viscosity mineral oil, glacial acetic acid added at an approximate concentration of 0.5% of the total volume and DMSO added at an approximate concentration of 1% of the total volume. Samples are heated at 65° C. in a commercial tissue microwave processor (H2800, Energy Beam Sciences ) for 5 minutes in a 1500 ml beaker containing the solution, which is agitated by bubbling.

Step 4.

Following microwave irradiation, impregnation is initiated by incubation in two baths of a wax solution of 30% low viscosity mineral oil and 70% molten paraffin placed in a large dessicator resting in a 60° C. glycerin bath, under a vacuum of about 640 mm of Hg, for 5 min. in each bath.

Step 5.

Impregnation is completed by incubation in four baths of molten paraffin placed within a large dessicator resting in a glycerin bath at about 75° C. to 80° C. and a reduced pressure of about 640 mm of Hg, for 5 min each. Tissue sections were transferred from one paraffin bath to the next at 5 min intervals, for a total impregnation time of 20 min. Each 5 min interval was measured for the time that the pressure reading is about 640 mm of Hg.

Example 4

Detection of Antigen in Tissue Sections

Paraffin sections are cut on a microtome to a thickness of 3 microns, placed in a water bath, and floated onto a glass slide. Paraffin was melted by placing slides in either a 58° C. oven for 30 minutes, or preferably in a 37° C. oven for approximately 18 hours or overnight, and then dewaxed in a xylene bath for 10 minutes. Slides were rehydrated in decreasing ethanol solutions for 1 min each (two baths of absolute, two baths of 95%, and one bath of 90%) and rinsed by submerging in tap water for 2 min.

Endogenous peroxidase was blocked with a solution of 6% hydrogen peroxide ($H_2O_2$) and methanol, or 35 ml of 6% $H_2O_2$ with 140 ml methanol, incubated for 15 min. Slides were rinsed by submerging in tap water for 2 min and PBS for 2 min, then dried.

Slides were transferred to a humidity chamber and normal horse serum (NHS) was added to block for 10 min. Excess normal horse serum was decanted from slides, and specific primary antibody was incubated for 30 min on the tissue section in a humidity chamber at room temperature. Slides were flushed with PBS with back and forth motion using a squeeze bottle, submerged in a PBS bath for 2 min, and excess PBS was dried off each slide. Linking solution (also known as secondary antibody or biotinylated anti-rabbit or anti-mouse) was added to each tissue section and incubated for 25 min in a humidity chamber. Slides were flushed with PBS using a squeeze bottle, submerged in a PBS bath for 2 min, and excess PBS was dried off each slide.

Signal was developed according to manufacturer's instructions (Vector Laboratories). ABC solution was added to the tissue section and incubated for 25 min in humidity chamber. Slides were flushed with PBS in a squeeze bottle and submerged in a rack in a PBS bath for 2 min. The rack was submerged in a bath of DAB chromogen for 6 min, then submerged under running water to wash gently for 4 min. Tissue sections were counterstained with hematoxylin (staining time will depend on the age of the hematoxylin) from 15 sec to 90 sec. Slides were washed under running water for 3 min to remove excess counterstain, dehydrated in alcohol baths (about 10 sec in each) from 85% to 100%, cleaned in xylene, and coverslipped.

Better antigen reactivity has been shown for progesterone receptor, factor VIII-related antigen, CD-31, CD-68, cytokeratin-7, chromogranin, and smooth muscle antigen, probably because of better preservation of antigen.

| Reagents | Catalog # | Source |
|---|---|---|
| Microscope slides - snow coat X-TRA | 00206 | Surgipath |
| Elite ABC Kit (standard) | PK-6100 | Vector Laboratories |
| Biotinylated anti-mouse IgG (H & L) | BA-2000 | Vector Laboratories |
| Biotinylated anti-mouse IgM (H & L) | BA-2020 | Vector Laboratories |
| Biotinylated anti-mouse/anti-rabbit IgG (H & L) | BA-6000 | Vector Laboratories |
| Normal horse serum (NHS) | S-2000 | Vector Laboratories |
| Diaminobenzidine tetrahydrochloride | K3466 | DAKO Corporation |
| Potassium phosphate (monobasic) | 7100-500 NY | Baxter Scientific |
| Sodium phosphate (dibasic) | 7917-2.5 NY | Baxter Scientific |
| Sodium chloride (AR Crystals) | 7581-2.5 NY | Baxter Scientific |
| 30% Hydrogen peroxide | 5240-500 NY | Baxter Scientific |
| Xylene | 8644-20 NY | Baxter Scientific |
| Harris hematoxylin | S-7735-3 | Baxter Scientific |
| Methyl alcohol | 3016-20 NY | Baxter Scientific |
| 95% Alcohol | | Florida Distillers |
| Absolute Ethyl Alcohol | | Florida Distillers |

Antibodies, Dilutions and Incubation Times

| Rabbit (R) | Microwave (M) | 30' Incubation |
|---|---|---|
| Mouse (MIgG) | Trypsin (T) | 45' Incubation |
| Mouse (MIgM) | Protease (P) | 90' Incubation |
| Goat (G) | Fast Green (FG) | |

| Abbreviation | Antibody | Special Procedure | Incubation Time | Linking Solution |
|---|---|---|---|---|
| (ACTH) | Adrenocorticotropin Hormone | 1:2000 | 30' | R |
| (AACT) | Alpha-1 Antichymotrypsin | 1:50000 | 30' | R |
| (AAT) | Alpha-1 Antitrypsin | 1:2000 | 30' | R |
| (ADENO) | Adenoviurs | 1:1000 | 30' | MIgG |
| (AFP) | Alpha Fetoprotein | 1:2500 | 30' | R |
| (AEI/3) | Cytokeratin | 1:200 (M) | 45' | MIgG |
| (ALA) | Alpha Lactalbumin | 1:600 | 30' | R |
| (ACTIN) | Actin Muscle | 1:200 | 30' | MIgG |
| (APP-A4) | Anti-Alzheimer Precursor Protein A4 | 1:500 (M) | 45' | MIgG |
| (ASPE) | Aspergillus | 1:500 | 30' | R |
| (AR) | Androgen Receptor | 1:20 (M) (FG) | 45' | MIgG |
| (BCA) | B-Cell | 1:200 | 30' | MIgG |
| (bcl-2) | Anti-Human Oncoprotein | 1:100 (M) | 45' | MIgG |
| (BerEp4) | Human Epithelial Antigen | 1:25 | 30' | MIgG |
| (B72.3) | TAG72 Tumor-Associated Glycoprotein 72 | 1:100 | 30' | MIgG |
| (BLA36) | B Lymphocyte Antigen | 1:100 | 30' | MIgG |
| (CMV) | Cytomegalovirus | 1:50 (P) | 30' | MIgG |
| (CHRG) | Chromogranin | 1:50 | 30' | MIgG |
| (CALC) | Calcitonin | 1:2000 | 30' | R |
| (CEA) | Carcinoembryonic Antigen | 1:6000 | 30' | R |
| (CERb'B2) | c-erbB-2 Oncogene Mab1 | 1:1500 | 90' | R |

Antibodies, Dilutions and Incubation Times

| Abbreviation | Antibody | Special Procedure | Incubation Time | Linking Solution |
|---|---|---|---|---|
| (CATH) | Cathepsin D | 1:2000 (M) | 45' | R |
| (CAM 5.2) | Cytokeratin | 1:500 (M) | 45' | R |
| (CK 7) | Cytokeratin | 1:200 (M) | 45' | MIgG |
| (CK 20) | Cytokeratin | 1:25 (M) | 45' | MIgG |
| (COLL IV) | Collagen IV | 1:25 (P) | 30' | MIgG |
| (CA 125) | Anti-Human CA 125 (MII) | 1:20 (M) | 45' | MIgG |
| (CD 30) | Anti-Human Ki-1 Antigen (BER-H2) | 1:200 (M) | 45' | MIgG |
| (ER) | Estrogen Receptor | 1:50 (M) (FG) | 45' | MIgM |
| (FVIII) | Von Willebrand Factor | 1:50 (P) | 30' | MIgM |
| (FSH) | Follicle Stimulating Hormone | 1:3000 | 30' | R |
| (5 HT) | Serotonin | 1:50 | 30' | MIgM |
| (FXIII) | Anti-coagulation Factor | 1:1200 | 30' | R |
| (GAST) | Gastrin | 1:2000 | 30' | MIgM |
| (GFAP) | Glial Fibrillary Acidic Protein | 1:1500 | 30' | R |
| (GLUC) | Glucagon | 1:10000 | 30' | R |
| (GH) | Growth Hormone | 1:5000 | 30' | R |
| (GCDFP) | Gross Cystic Disease Fluid Protein | 1:250 | 30' | MIgM |
| (GRP) | Gastrin-Releasing Peptide | 1:1000 | 30' | R |
| (HMWK) | High Molecular Weight Keratin (34 βE12) | 1:10 | 45' | MIgM |
| (Hbcore) | Hepatitis B Core Antigen | 1:5000 | 30' | R |
| (HBsAg) | Hepatitis B Surface Antigen | 1:100 | 30' | MIgM |
| (HSV I) | Herpes Simplex Type I | 1:10 | 30' | R |
| (HSV II) | Herpes Simplex Type II | 1:10 | 30' | R |
| (HCG) | Human Chorionic Gonadotropin | 1:50000 | 30' | R |
| (HPL) | Human Placental Lactogen | 1:100000 | 30' | R |

Antibodies, Dilutions and Incubation Times

| Abbreviation | Antibody | Special Procedure | Incubation Time | Linking Solution |
|---|---|---|---|---|
| (HIST) | Histoplasma | 1:1000 | 30' | R |
| (H.Pyl) | Heliobacter pylori | 1:500 (M) | 45' | R |
| (β-HCG) | β-Human Chorionic Gonadotropin | 1:10000 | 30' | R |
| (IgA) | Alpha Heavy Chain | 1:400 | 30' | R |

Antibodies, Dilutions and Incubation Times

-continued

| Abbreviation | Antibody | Special Procedure | Incubation Time | Linking Solution |
|---|---|---|---|---|
| (IgG) | Gamma Heavy Chain | 1:1000 | 30' | R |
| (IgAs) | Secretory Piece of IgA | 1:200 | 30' | R |
| (IgM) | Mu Heavy Chain IgM | 1:1000 | 30' | R |
| (INS) | Insulin | 1:100 | 30' | R |
| (Ki-67) | Nuclear Antigen MIB-1 | 1:50 (M) (FG) | 45' | MIgG |
| (K) | Kappa Light Chain | 1:200 (M) | 45' | MIgG |
| (KERATIN) | AEI/3 CAM | 1:50/1:500 (M) | 45' | MIgG |
| (LCA) | Leucocyte Common Antigen | 1:50 | 30' | MIgG |
| (Leu M1) | Leu M1 Antigen | 1:200 (M) | 45' | MIgM |
| (Leu 7) | Leu 7 Antigen | 1:50 (M) | 45' | MIgM |
| (Lectin) | Lectin | 1:4000 | USE INSTEAD OF NHS | |
| (Anti-Lectin) | Anti-Lectin Antigen | 1:10000 | 30' | G |
| (LEA 135) | Anti-Human Luminal Epithelial Antigen | 1:50 | 30' | MIgG |
| (LH) | Luteinizing Hormone | 1:3000 | 30' | R |
| (L) | Lambda Light Chain | 1:6000 (M) | 45' | MIgG |
| (LMK-8) | Low Molecular Weight Keratin | 1:25 (M) | 45' | MIgG |
| (LIP-AS 105) | Lipase | 1:400 | 30' | MIgG |
| (MCA) | Myeloid Histiocyte Antigen (MAC 387) | 1:400 (M) | 45' | MIgG |
| (MUR) | Muramidase | 1:2000 | 30' | R |
| (MYOGL) | Myoglobin | 1:5000 | 30' | R |
| (MAPH) | Macrophage | 1:50 | 30' | MIgG |

Antibodies, Dilutions and Incubation Times

| Abbreviation | Antibody | Special Procedure | Incubation Time | Linking Solution |
|---|---|---|---|---|
| (MTLT) | Metallothionein | 1:50 | 30' | MIgG |
| (MEL) | Melanoma HMB 45 | 1:50 | 30' | MIgG |
| (MAK 6) | Anti-Cytokeratin | 1:50 (T) | 90' | MIgG |
| (MBP) | Myelin | 1:500 | 30' | R |
| (MESO) | Mesothelial Antigen | 1:500 | 30' | MIgM |
| (MAST-C) | Mast Cell | 1:2000 (T) | 30' | MIgG |
| (MPO) | Myeloperoxidase | 1:5000 | 30' | R |
| (MGN) | Myogenin | 1:15 | 45' | MIgG |
| (NB) | Neuroblastoma | 1:200 | 90' | MigG |
| (N-FIL) | N-Filament (2F11) | 1:250 | 30' | MigG |
| (NSE) | Neuron Specific Enolase | 1:4000 (M) | 45' | MigG |
| (PAMYL) | Pancreatic Amylase | 1:20 | 30' | MigG |
| (PCP) | Pneumocystis carinii | 1:25 | 30' | MigM |
| (PLAP) | Placental Alkaline Phosphatase | 1:800 | 30' | R |
| (PPP) | Pancreatic Polypeptide | 1:3000 | 30' | R |
| (PTH) | Parathyroid Hormone | 1:250 (M) | 45' | (RAT) |
| (PROL) | Prolactin | 1:500 | 30' | R |
| (PAPH) | Prostatic Acid Phosphatase | 1:4000 | 30' | R |
| (PML) (SV4O) | Progressive Multifocal Leucoencephalopathy | 1:10000 | 30' | R |
| (PR) | Progesterone Receptor | 1:100 (M) | 45' | R |
| (PR 1A6) | Progesterone Receptor | 1:50 (M) | 45' | MigG |
| (PSA) | Prostate Specific Antigen | 1:750 | 30' | R |
| (PCNA) | Proliferating Cell Nuclear | 1:100 (M) (FG) | 45' | MigG |
| (PS2) | PS2 Protein | 1:1000 | 45' | R |
| (P53) | p53 Antigen | 1:50 (M) (FG) | 45' | MigG |

Antibodies, Dilutions and Incubation Times

| Abbreviation | Antibody | Special Procedure | Incubation Time | Linking Solution |
|---|---|---|---|---|
| (S100 A) | S100 A Protein | 1:3000 | 30' | R |
| (S100) | S100 Protein | 1:2000 | 30' | R |
| (SOMAT) | Somatostatin | 1:3000 | 30' | R |
| (SYNAP) | Synaptophysin | 1:800 (M) | 45' | R |
| (SMA) | Smooth Muscle Actin | 1:100 | 30' | MigG |
| (SR-1) | Sarcomeric Actin | 1:100 | 30' | MigG |
| (TESTOS) | Testosterone | 1:250 | 30' | R |
| (TGB) | Thyroglobulin | 1:20000 | 30' | R |
| (TP-103) | Treponema | 1:50 (T) | 30' | MigG |
| (TM) | Thrombomodulin | 1:50 | 30' | MigG |
| (TSH) | Thyroid Stimulating Hormone | 1:2000 | 30' | R |
| (TCA) | T-Cell Antigen | 1:800 (M) | 45' | MigG |
| (TOXO) | Toxoplasma | 1:1000 | 30' | R |
| (UBT) | Ubiquitin | 1:250 | 30' | R |
| (VIP) | Vasoactive intestinal peptide | 1:1500 | 30' | R |
| (VIM) | Vimentin | 1:800 (M) | 45' | MigG |
| (VZV) | Variecella-Zoster Virus | 1:100 | 30' | MigG |
| (WSKER) | Wide Spectrum Keratin | 1:500 | 30' | R |

Example 5
DNA Extraction from Processed Tissue Sections

Two six micron tissue sections were placed in a 1.5 ml microfuge tube, 800 μl xylene was added and mixed by vortexing, 400 μl absolute ethanol was added and mixed by vortexing, the tube was centrifuged for 5 minutes in a high speed microfuge, and the supernatant was decanted. To the pellet, 800 μl absolute ethanol was added and mixed by vortexing.

The supernatant was decanted after centrifugation as above, and 100 μl of a detergent/proteinase K solution (1% NP40 or Triton X-100, 2.4 μl of 2.5 mg/ml proteinase K) was added to the pellet and incubated at 55° for one hour. Proteinase K was inactivated by incubation at 95° for 10 min. Save the supernatant containing DNA after centrifugation in the microfuge for 5 min. This material is ready for PCR. It should be precipitated and/or extracted further if Southern blotting is planned. More sections would be required to obtain enough DNA for restriction analysis.

Figure 13A:
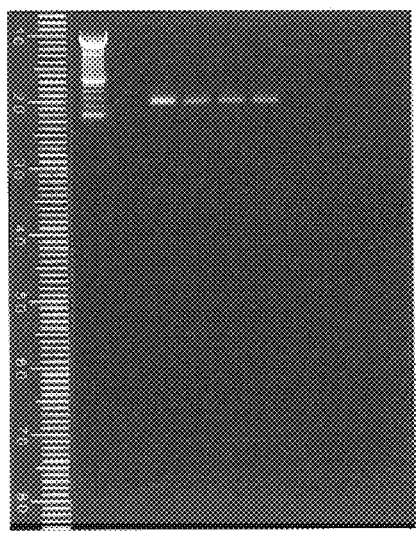
FIGS. 13A–13B show agarose gel electrophoresis of DNA and RNA, respectively, prepared from processed tissue specimens.

FIG. 13A shows the quantity and quality of polymerase chain reaction (PCR) amplified DNA are comparable between samples prepared according to the present invention (Example 1) and by conventional tissue processing (Tissue-Tek VIP histoprocessor, Miles-Sakura, used according to manufacturer's instructions).

Example 6
RNA Extraction from Processed Tissue Sections

Ten sections (7 μm each) of a paraffin block were cut using disposable blades; the blocks were prepared according to the present invention and by conventional tissue processing as described in Example 5. They were placed in 50 ml Falcon tubes, deparaffinized with 20 ml of xylene, and the remaining tissue was then washed twice with absolute alcohol for 30 minutes. The tissue was suspended at 0.5 g/ml in a solution containing 4M guanidinium thiocyanate, 25 mM Na citrate pH 7.0, 0.5% N-laurylsarcosine, and 0.1 M of 2-mercaptoethanol. The solution was mixed by vortexing and DNA was sheared by passage through an 18 to 22 gauge syringe needle.

Figure 13B:
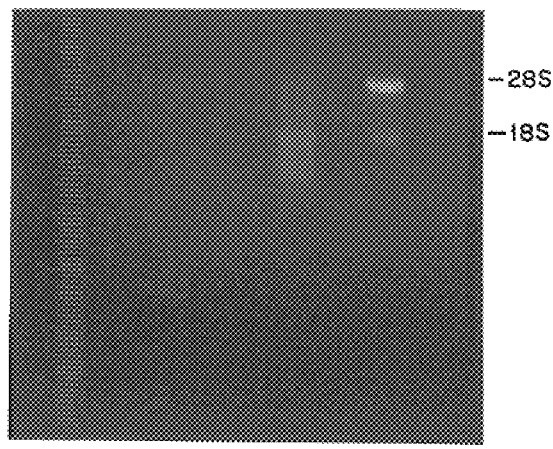

The RNA-containing solution was carefully layered on 2.8 ml of 5.7 M CsCl in several 5 ml centrifuge tubes (Sorvall), and RNA was sedimented by centrifugation in an SW55Ti rotor at 35,000 rpm and 18° C. for 14 hours in a Beckman L8-53 ultracentrifuge. The top fraction was carefully removed to leave an RNA pellet at the bottom of the tube. The pellet was resuspended with ribonuclease-free water, and the Eppendorf tube was spun at 14,000 rpm for 10 min. The supernatant containing RNA was saved and the UV absorbance was measured: extinction coefficient 1 $OD_{280}$/cm is 40 µg/ml RNA, $OD_{260}/OD_{280}$ ratio should be between about 1.8 and about 2.0. A total of 45 µg RNA was extracted from tissue specimens prepared according to the present invention whereas no RNA was detectable from tissue specimens processed conventionally (FIG. 13B).

While the present invention has been described in connection with what is presently considered to be practical and preferred embodiments, it is understood that the present invention is not to be limited or restricted to the disclosed embodiments but, on the contrary, is intended to cover various modifications and equivalent arrangements included within the spirit and scope of the appended claims.

Thus, it is to be understood that variations in the described invention will be obvious to those skilled in the art without departing from the novel aspects of the present invention and such variations are intended to come within the scope of the claims below.

We claim:

1. A method of processing a tissue specimen for histology comprising:
   (a) slicing a solid tissue to provide at least one tissue specimen to a thickness of up to 2 mm,
   (b) fixing the tissue specimen,
   (c) dehydrating the tissue specimen,
   (d) removing fat from the tissue specimen,
   (e) impregnating the tissue specimen with a mixture of waxes having different melting points to provide a block comprised of the tissue specimen and wax, and
   (f) sectioning the block to provide a tissue section which is only then placed on a slide;
   wherein said tissue specimen is processed in steps (b)–(d) by a series of all non-aqueous solutions, at least one of which is a first solution comprising fixative and dehydrating agent;
   wherein fixation, dehydration, and fat removal occur with agitation of said non-aqueous solutions and heating by microwave energy;
   wherein impregnation is conducted under less than atmospheric pressure; and
   whereby said tissue specimen is fixed, dehydrated, defatted, and impregnated in about 90 minutes or less.

2. A method of continuous tissue processing for histology comprising:
   (a) providing a series of tissue specimens up to 1.5 mm in thickness,
   (b) fixing at least one of said tissue specimens,
   (c) dehydrating at least one of said tissue specimens,
   (d) removing fat from at least one of said tissue specimens, and
   (e) impregnating at least one of said tissue specimens under less than atmospheric pressure with a mixture of waxes having different melting points, wherein steps (b)–(e) are completed in about 90 minutes or less;
   wherein all solutions for processing said tissue specimens are non-aqueous and said series of tissue specimens is processed by initiating step (b) for a later-processed tissue specimen before step (e) for an earlier-processed tissue specimen has been completed, and
   wherein steps (b), (c), and (d) occur with agitation and heating by microwave energy.

3. A method of continuous tissue processing for histology comprising:
   (a) slicing a solid tissue to provide a tissue specimen of up to 2 mm in thickness,
   (b) fixing and dehydrating said tissue specimen by incubation in a series of all non-aqueous solutions with agitation and heating by microwave energy,
   (c) impregnating said fixed and dehydrated tissue specimen under less than atmospheric pressure, and
   (d) repeating steps (b) and (c) at least once with another tissue specimen, wherein at least one repetition of steps (b) and (c) takes about 90 minutes or less;
   whereby tissue specimens are continuously processed by initiating step (b) for a later-processed tissue specimen before step (c) has been completed for an earlier-processed tissue specimen.

4. A method according to claim 3, wherein said tissue specimen is sliced to a thickness between 1 mm and 2 mm before processing.

5. A method according to claim 3, wherein said tissue specimen is sliced to a thickness between 1 mm and 1.5 mm before processing.

6. A method according to claim 3 further comprising sectioning said fixed, dehydrated, and impregnated tissue specimen to provide a tissue section of between 1 micron and 50 microns.

7. The method of claim 3, wherein at least one of said series of non-aqueous solutions is a first solution comprised of fixative and dehydrating agent.

8. The method of claim 7, wherein said tissue specimen is incubated in said first solution for at least 15 minutes.

9. The method of claim 7, wherein said first solution is comprised of alcohol and ketone.

10. The method of claim 9, wherein said first solution contains a volume ratio of alcohol to ketone between 1:1 and 3:1.

11. The method of claim 7, wherein said first solution is further comprised of polymers between 100 and 500 average molecular weight.

12. The method of claim 11, wherein said first solution is further comprised of a surfactant at about 1% of total volume.

13. The method of claim 3, wherein at least one of said series of non-aqueous solutions is a first solution comprised of acetone, isopropyl alcohol, and low molecular weight polyethylene glycol.

14. The method of claim 3 further comprising clearing said tissue specimen in a non-aqueous solution comprised of clearant.

15. The method of claim 14, wherein said clearant is xylene.

16. The method of claim 3, wherein tissue specimens are processed without using formalin.

17. The method of claim 3, wherein tissue specimens are processed without using xylene.

18. The method of claim 3, wherein at least one of said series of non-aqueous solutions is comprised of alcohol, ketone, and mineral oil.

19. The method of claim 3, wherein said fixed and dehydrated tissue specimen is impregnated with a mixture of waxes having different melting points.

20. The method of claim 3, wherein said fixed and dehydrated tissue specimen is impregnated with a wax solution comprised of xylene and paraffin.

21. The method of claim 3, wherein said fixed and dehydrated tissue specimen is impregnated with a wax solution comprised of mineral oil and paraffin.

22. The method of claim 3, wherein said fixed and dehydrated tissue specimen is impregnated in molten paraffin for at least 12 minutes.

23. A method of continuous tissue processing for histology comprising:
   (a) slicing a solid tissue to provide tissue specimens with thickness between 1 mm and 2 mm, wherein a tissue specimen to be processed is not placed on a slide for histology until said tissue specimen has been hardened, impregnated, and sectioned;
   (b) hardening said tissue specimen by incubation in a series of all non-aqueous solutions with agitation and heating by microwave energy, wherein incubation in a first non-aqueous solution comprised of ketone and alcohol is then followed by incubation in a second non-aqueous solution comprised of less concentrated ketone and more concentrated alcohol as compared to said first non-aqueous solution;
   (c) impregnating said hardened tissue specimen in a wax solution under less than atmospheric pressure to provide a block comprised of said hardened and impregnated tissue specimen and wax, wherein hardening and impregnating a tissue specimen takes about 90 minutes or less; and
   (d) repeating steps (b) and (c) at least once with another tissue specimen;
   whereby tissue specimens are continuously processed by initiating hardening of a later-processed tissue specimen before impregnation of an earlier-processed tissue specimen has been completed.

24. A method according to claim 23 further comprising sectioning said hardened and impregnated tissue specimen to provide a tissue section of between 1 micron and 50 microns.

25. The method of claim 23 further comprising placing said tissue section on a slide for histology, and then removing wax from the slide.

26. The method of claim 23, wherein said tissue specimen is incubated in said first non-aqueous solution for at least 15 minutes.

27. The method of claim 23, wherein said first non-aqueous solution is comprised of acetone and isopropyl alcohol.

28. The method of claim 27, wherein said first non-aqueous solution contains a volume ratio of alcohol to ketone between 1:1 and 3:1.

29. The method of claim 23, wherein said first non-aqueous solution is further comprised of polymers between 100 and 500 average molecular weight.

30. The method of claim 29, wherein said first non-aqueous solution is further comprised of a surfactant at about 1% of total volume.

31. The method of claim 23, wherein said first non-aqueous solution is comprised of acetone, isopropyl alcohol, and low molecular weight polyethylene glycol.

32. The method of claim 23 further comprising clearing said tissue specimen in a non-aqueous solution comprised of clearant.

33. The method of claim 32, wherein said clearant is xylene.

34. The method of claim 23, wherein tissue specimens are processed without using formalin.

35. The method of claim 23, wherein tissue specimens are processed without using xylene.

36. The method of claim 23, wherein at least one of said series of non-aqueous solutions is comprised of alcohol, ketone, and mineral oil.

37. The method of claim 23, wherein said fixed and dehydrated tissue specimen is impregnated with a mixture of waxes having different melting points.

38. The method of claim 23, wherein said fixed and dehydrated tissue specimen is initially impregnated with a wax solution comprised of xylene and paraffin.

39. The method of claim 23, wherein said fixed and dehydrated tissue specimen is impregnated with a wax solution comprised of mineral oil and paraffin.

40. The method of claim 23, wherein said fixed and dehydrated tissue specimen is impregnated in molten paraffin for at least 12 minutes.

* * * * *